(12) United States Patent
Dhodapkar et al.

(10) Patent No.: US 9,808,504 B2
(45) Date of Patent: Nov. 7, 2017

(54) IMMUNOGENIC EPITOPES AS TARGETS FOR UNIVERSAL CANCER VACCINES

(75) Inventors: Kavita Dhodapkar, New Haven, CT (US); Madhav Dhodapkar, New Haven, CT (US)

(73) Assignee: Yale University, New Haven, CT (US)

( * ) Notice: Subject to any disclaimer, the term of this patent is extended or adjusted under 35 U.S.C. 154(b) by 1178 days.

(21) Appl. No.: 13/387,676

(22) PCT Filed: Sep. 22, 2010

(86) PCT No.: PCT/US2010/049823
§ 371 (c)(1),
(2), (4) Date: Apr. 19, 2012

(87) PCT Pub. No.: WO2011/038002
PCT Pub. Date: Mar. 31, 2011

(65) Prior Publication Data
US 2012/0207775 A1  Aug. 16, 2012

Related U.S. Application Data

(60) Provisional application No. 61/277,285, filed on Sep. 22, 2009.

(51) Int. Cl.
*A61K 39/00* (2006.01)
*A61K 38/17* (2006.01)
*A61K 39/39* (2006.01)

(52) U.S. Cl.
CPC ...... *A61K 38/1709* (2013.01); *A61K 39/0011* (2013.01); *A61K 39/39* (2013.01)

(58) Field of Classification Search
None
See application file for complete search history.

(56) References Cited

U.S. PATENT DOCUMENTS

| | | | |
|---|---|---|---|
| 4,082,735 A | 4/1978 | Jones et al. | |
| 4,082,736 A | 4/1978 | Jones et al. | |
| 4,101,536 A | 7/1978 | Yamamura et al. | |
| 4,185,089 A | 1/1980 | Derrien et al. | |
| 4,235,771 A | 11/1980 | Adam et al. | |
| 4,406,890 A | 9/1983 | Tarcsay et al. | |
| 4,606,918 A | 8/1986 | Allison et al. | |
| 4,683,202 A | 7/1987 | Mullis | |
| 4,962,091 A | 10/1990 | Eppstein et al. | |
| 5,350,674 A | 9/1994 | Boenisch et al. | |
| 5,585,362 A | 12/1996 | Wilson et al. | |
| 5,928,906 A | 7/1999 | Koster et al. | |
| 6,326,193 B1 | 12/2001 | Liu et al. | |
| 2004/0180347 A1 | 9/2004 | Standon et al. | |
| 2005/0260623 A1 | 11/2005 | Trosko et al. | |
| 2005/0277162 A1* | 12/2005 | Gudas | G01N 33/574 435/7.23 |
| 2008/0234183 A1* | 9/2008 | Hallbrink | A61K 51/0448 514/1.1 |
| 2008/0260762 A1 | 10/2008 | Grey et al. | |

FOREIGN PATENT DOCUMENTS

| | | | |
|---|---|---|---|
| WO | WO 94/07529 | 4/1994 | |
| WO | WO 00/06723 | 10/2000 | |
| WO | WO 01/29058 | 4/2001 | |
| WO | WO 01/96584 | 12/2001 | |
| WO | WO 2007/010287 A1 * | 1/2007 | |
| WO | WO 2009/007852 A1 * | 1/2009 | |

OTHER PUBLICATIONS

Uniprot Q01860, 1993.*
Hammer et al. (J. Exp. MEd. 1992, 176: 1007-1013).*
Thibodeau (Oncolmmunology 1:6, 908-916; Sep. 2012, Landes Bioscience).*
Karin et al (J.Exp. Med., 1994, 180: 2227-2237).*
Mirriam-Webster Dictionary, 2015, 4 pages.*
Berger et al (Int. J. Cancer. 111: 229-237, 2004).*
Celis (J. Clin. Invest. 2002, 110(12: 1765-1768).*
Marchand et al (Int. J. Cancer 80: 219-230, 1999).*
Marchand et al (Exp. Opin. Biol. Ther. 1(3): 497-510, 2001).*
Bodey et al (Anticancer Research 20: 2665-2676, 2000).*
Gao et al (J. Immunother. 23: 643-653, 2000).*
Boon et al (Ann. Rev. Immunol. 2006, 24: 175-208).*
Gregory et al (Front. Cell. Infect. Microbiol, 2013, vol. 3, Article 13, pp. 1-13, frontiersin.org).*
Ben-Porath et al., Nat Genet, 40:499-507 (2008) "An embryonic stem cell-like gene expression signature in poorly differentiated aggressive human tumors."
Boyer et al., Cell, 122:947-956 (2005) "Core Transcriptional Regulatory Circuitry in Human Embryonic Stem Cells".
Chang et al., J Exp Med, 201(9):1503-1517 (2005) "Sustained expansion of NKT cells and antigen-specific T cells after injection of α-galactosyl-ceramide loaded mature dendritic cells in cancer patients".
Corthay et al., Immunity, 22:371-383 (2005) "Primary Antitumor Immune Response Mediated by CD4+ T Cells".
Gidekel et al., Cancer Cell, 4:361-370 (2003) "Oct-3/4 is a dose-dependent oncogenic fate determinant".
Glinsky, J. Clin. Oncology, 26:2846-2853 (2008) ""Sternness" genomics law governs clinical behavior of human cancer: implications for decision making in disease management", abstract only.
Ji et al., PLoS One, 4:e8065 (2009) "Pluripotent Transcription Factors Possess Distinct Roles in Normal versus Transformed Human Stem Cells".
Masters et al., Nat Rev Cancer, 3:517-525 (2003) "Curing metastatic cancer: lessons from testicular germ-cell tumours", abstract only.
Miura et al., Nat Biotechnol, 27:743-745 (2009) "Variation in the safety of induced pluripotent stem cell lines", abstract only.
Mumberg et al., Proc Natl Acad Sci USA, 96:8633-8638 (1999) "CD4+ T cells eliminate MHC class II-negative cancer cells in vivo by indirect effects of IFN-γ".

(Continued)

*Primary Examiner* — Gerald R Ewoldt
*Assistant Examiner* — Marianne Dibrino
(74) *Attorney, Agent, or Firm* — Saul Ewing Arnstein & Lehr LLP; Kathryn Doyle

(57) ABSTRACT

The present invention provides a peptide having an amino acid sequence as set forth in SEQ ID NOs: 1 through 95 and any combination thereof. The peptide or combination of peptides possess OCT4 specific inducibility. The peptide or combination of peptides can further be used as a vaccine.

4 Claims, 6 Drawing Sheets

(56) References Cited

OTHER PUBLICATIONS

Nouri et al., Eur J. Cancer, 29A:1895-1899 (1993) "Immunological paradox in testicular tumours: the presence of a large number of activated T-cells despite the complete absence of MHC antigens", abstract.
Pardoll et al., Curr Opin Immunol, 10:588-594 (1998) "The role of CD4+ T cell responses in antitumor immunity", abstract only.
Reya et al., Nature, 414:105-111 (2001) "Stem cells, cancer, and cancer stem cells", abstract only.
Schoehals et al., Biochem Biophys Res Commun, 383:157-162 (2009) "Embryonic stem cell markers expression in cancers", abstract only.
Takahashi et al., Cell 131:861-871 (2007) "Induction of Pluripotent Stem Cells from Adult Human Fibroblasts by Defined Factors".
Utikal et al., Nature 460:1145-1148 (2009) "Immortalization eliminates a roadblock during cellular reprogramming into iPS cells".
Wang et al., Cell Stem, Cell, 2:297-299 (2008) "Cancer: Inappropriate Expression of Stem Cell Programs?"
Zitvogel et al., Nat Rev Immunol, 8:59-73 (2008) "Immunological aspects of cancer chemotherapy".
International Search Report for PCT/US10/49823 dated Nov. 26, 2010.
Dhodapkar et al., Proc Natl Acad Sci USA, 107:8718-8723 (2010) "Natural immunity to pluripotency antigen OCT4 in humans".
Krizhanovsky et al., Nature 460:1085-1086 (2009) "The promises and perils of p53", abstract only.
Brewer et al., "Embryonic vaccines against cancer: an early history." 2009, Exp Mol Pathol 86:192-7.
Cicinnati et al., "Increased frequencies of CD8+ T lymphocytes recognizing wild-type p53-derived epitopes in peripheral blood correlate with presence of epitope loss tumor variants in patients with hepatocellular carcinoma." 2006, Int J Cancer 119:2851-60.
De Jong et al., "Stem cell marker OCT3/4 in tumor biology and germ cell tumor diagnostics: history and future." 2006, Crit Rev Oncog 12:171-203.
Dhodapkar et al., "Antitumor monoclonal antibodies enhance cross-presentation ofcCellular antigens and the generation of myeloma-specific killer T cells by dendritic cells." 2002, J Exp Med 195:125-33.
Dhodapkar et al., "Natural immunity to pluripotency antigen OCT4 in humans." 2010, Proc Natl Acad Sci USA 107(19):8718-23.
Knoepfler, "Deconstructing stem cell tumorigenicity: a roadmap to safe regenerative medicine." 2009, Stem Cells 27:1050-56.
Kordes et al., "Hepatic and pancreatic stellate cells in focus." 2009, Biol Chem 390:1003-12.
Lengner et al., "Oct4 expression is not required for mouse somatic stem cell self-renewal." 2007, Cell Stem Cell 1:403-15.
Li et al., "Vaccination with human pluripotent stem cells generates a broad spectrum of immunological and clinical responses against colon cancer." 2009, Stem Cells 27:3103-11.
Lui et al., "Embryonic stem cells: overcoming the immunological barriers to cell replacement therapy." 2009, Curr Stem Cell Res Ther 4:70-80.
Monti et al., "Evidence for in vivo primed and expanded autoreactive T cells as a specific feature of patients with type 1 diabetes." 2007, J Immunol 179:5785-92.
Pickford et al., "Different forms of helper tolerance to carcinoembryonic antigen: ignorance and regulation." 2007, Clin Cancer Res 13:4528-37.
Pittet et al., "High frequencies of naive Melan-A/MART-1-specific CD8(+) T cells in a large proportion of human histocompatibility leukocyte antigen (HLA)-A2 individuals." 1999, J Exp Med 190:705-15.
Shin et al., "Novel epigenetic mechanisms that control pluripotency and quiescence of adult bone marrow-derived Oct4(+) very small embryonic-like stem cells." 2009, Leukemia 23:2042-51.
Spisek et al., "Frequent and specific immunity to the embryonal stem cell-associated antigen SOX2 in patients with monoclonal gammopathy." 2007, J Exp Med 204(4):83140.
Vella et al., "Healthy individuals have T-cell and antibody responses to the tumor antigen cyclin B1 that when elicited in mice protect from cancer." 2009, Proc Natl Acad Sci USA 106:14010-15.
Yamanaka, "A fresh look at iPS cells." 2009, Cell 137:13-17.

* cited by examiner

```
SEQUENCE LISTING

<160> NUMBER OF SEQ ID NOS: 95

<210> SEQ ID NO 1
<211> LENGTH: 15
<212> TYPE: PRT
<213> ORGANISM: Artificial
<220> FEATURE:
<223> OTHER INFORMATION: Synthetic Construct

<400> SEQUENCE: 1

Met Ala Gly His Leu Ala Ser Asp Phe Ala Phe Ser Pro Pro Pro
1               5                   10                  15

<210> SEQ ID NO 2
<211> LENGTH: 15
<212> TYPE: PRT
<213> ORGANISM: Artificial
<220> FEATURE:
<223> OTHER INFORMATION: Synthetic Construct

<400> SEQUENCE: 2

Leu Ala Ser Asp Phe Ala Phe Ser Pro Pro Pro Gly Gly Gly Gly
1               5                   10                  15

<210> SEQ ID NO 3
<211> LENGTH: 14
<212> TYPE: PRT
<213> ORGANISM: Artificial
<220> FEATURE:
<223> OTHER INFORMATION: Synthetic Construct

<400> SEQUENCE: 3

Phe Ala Phe Ser Pro Pro Pro Gly Gly Gly Gly Asp Gly Pro
1               5                   10

<210> SEQ ID NO 4
<211> LENGTH: 14
<212> TYPE: PRT
<213> ORGANISM: Artificial
<220> FEATURE:
<223> OTHER INFORMATION: Synthetic Construct
```

-continued

```
<400> SEQUENCE: 4

Ser Pro Pro Pro Gly Gly Gly Asp Gly Pro Gly Pro
1               5                   10

<210> SEQ ID NO 5
<211> LENGTH: 15
<212> TYPE: PRT
<213> ORGANISM: Artificial
<220> FEATURE:
<223> OTHER INFORMATION: Synthetic Construct

<400> SEQUENCE: 5

Pro Gly Gly Gly Gly Asp Gly Pro Gly Gly Pro Glu Pro Gly Trp
1               5                   10                  15

<210> SEQ ID NO 6
<211> LENGTH: 15
<212> TYPE: PRT
<213> ORGANISM: Artificial
<220> FEATURE:
<223> OTHER INFORMATION: Synthetic Construct

<400> SEQUENCE: 6

Gly Asp Gly Pro Gly Gly Pro Glu Pro Gly Trp Val Asp Pro Arg
1               5                   10                  15

<210> SEQ ID NO 7
<211> LENGTH: 15
<212> TYPE: PRT
<213> ORGANISM: Artificial
<220> FEATURE:
<223> OTHER INFORMATION: Synthetic Construct

<400> SEQUENCE: 7

Gly Gly Pro Glu Pro Gly Trp Val Asp Pro Arg Thr Trp Leu Ser
1               5                   10                  15

<210> SEQ ID NO 8
<211> LENGTH: 15
<212> TYPE: PRT
<213> ORGANISM: Artificial
<220> FEATURE:
<223> OTHER INFORMATION: Synthetic Construct

<400> SEQUENCE: 8

Pro Gly Trp Val Asp Pro Arg Thr Trp Leu Ser Phe Gln Gly Pro
1               5                   10                  15

<210> SEQ ID NO 9
<211> LENGTH: 15
<212> TYPE: PRT
<213> ORGANISM: Artificial
<220> FEATURE:
<223> OTHER INFORMATION: Synthetic Construct

<400> SEQUENCE: 9

Asp Pro Arg Thr Trp Leu Ser Phe Gln Gly Pro Pro Gly Gly Pro
1               5                   10                  15

<210> SEQ ID NO 10
<211> LENGTH: 15
<212> TYPE: PRT
<213> ORGANISM: Artificial
<220> FEATURE:
<223> OTHER INFORMATION: Synthetic Construct

<400> SEQUENCE: 10
```

```
Trp Leu Ser Phe Gln Gly Pro Pro Gly Gly Pro Gly Ile Gly Pro
1               5                   10                  15

<210> SEQ ID NO 11
<211> LENGTH: 14
<212> TYPE: PRT
<213> ORGANISM: Artificial
<220> FEATURE:
<223> OTHER INFORMATION: Synthetic Construct

<400> SEQUENCE: 11

Phe Gln Gly Pro Pro Gly Gly Pro Gly Ile Gly Pro Gly Val
1               5                   10

<210> SEQ ID NO 12
<211> LENGTH: 15
<212> TYPE: PRT
<213> ORGANISM: Artificial
<220> FEATURE:
<223> OTHER INFORMATION: Synthetic Construct

<400> SEQUENCE: 12

Pro Pro Gly Gly Pro Gly Ile Gly Pro Gly Val Gly Pro Gly Ser
1               5                   10                  15

<210> SEQ ID NO 13
<211> LENGTH: 14
<212> TYPE: PRT
<213> ORGANISM: Artificial
<220> FEATURE:
<223> OTHER INFORMATION: Synthetic Construct

<400> SEQUENCE: 13

Pro Gly Ile Gly Pro Gly Val Gly Pro Gly Ser Glu Val Trp
1               5                   10

<210> SEQ ID NO 14
<211> LENGTH: 15
<212> TYPE: PRT
<213> ORGANISM: Artificial
<220> FEATURE:
<223> OTHER INFORMATION: Synthetic Construct

<400> SEQUENCE: 14

Gly Pro Gly Val Gly Pro Gly Ser Glu Val Trp Gly Ile Pro Pro
1               5                   10                  15

<210> SEQ ID NO 15
<211> LENGTH: 15
<212> TYPE: PRT
<213> ORGANISM: Artificial
<220> FEATURE:
<223> OTHER INFORMATION: Synthetic Construct

<400> SEQUENCE: 15

Gly Pro Gly Ser Glu Val Trp Gly Ile Pro Pro Cys Pro Pro Pro
1               5                   10                  15

<210> SEQ ID NO 16
<211> LENGTH: 15
<212> TYPE: PRT
<213> ORGANISM: Artificial
<220> FEATURE:
<223> OTHER INFORMATION: Synthetic Construct

<400> SEQUENCE: 16
```

```
Glu Val Trp Gly Ile Pro Pro Cys Pro Pro Tyr Glu Phe Cys
1               5                  10                 15
```

<210> SEQ ID NO 17
<211> LENGTH: 15
<212> TYPE: PRT
<213> ORGANISM: Artificial
<220> FEATURE:
<223> OTHER INFORMATION: Synthetic Construct

<400> SEQUENCE: 17

```
Ile Pro Pro Cys Pro Pro Pro Tyr Glu Phe Cys Gly Gly Met Ala
1               5                  10                 15
```

<210> SEQ ID NO 18
<211> LENGTH: 15
<212> TYPE: PRT
<213> ORGANISM: Artificial
<220> FEATURE:
<223> OTHER INFORMATION: Synthetic Construct

<400> SEQUENCE: 18

```
Pro Pro Pro Tyr Glu Phe Cys Gly Gly Met Ala Tyr Cys Gly Pro
1               5                  10                 15
```

<210> SEQ ID NO 19
<211> LENGTH: 15
<212> TYPE: PRT
<213> ORGANISM: Artificial
<220> FEATURE:
<223> OTHER INFORMATION: Synthetic Construct

<400> SEQUENCE: 19

```
Glu Phe Cys Gly Gly Met Ala Tyr Cys Gly Pro Gln Val Gly Val
1               5                  10                 15
```

<210> SEQ ID NO 20
<211> LENGTH: 15
<212> TYPE: PRT
<213> ORGANISM: Artificial
<220> FEATURE:
<223> OTHER INFORMATION: Synthetic Construct

<400> SEQUENCE: 20

```
Gly Met Ala Tyr Cys Gly Pro Gln Val Gly Val Gly Leu Val Pro
1               5                  10                 15
```

<210> SEQ ID NO 21
<211> LENGTH: 15
<212> TYPE: PRT
<213> ORGANISM: Artificial
<220> FEATURE:
<223> OTHER INFORMATION: Synthetic Construct

<400> SEQUENCE: 21

```
Cys Gly Pro Gln Val Gly Val Gly Leu Val Pro Gln Gly Gly Leu
1               5                  10                 15
```

<210> SEQ ID NO 22
<211> LENGTH: 14
<212> TYPE: PRT
<213> ORGANISM: Artificial
<220> FEATURE:
<223> OTHER INFORMATION: Synthetic Construct

<400> SEQUENCE: 22

```
Val Gly Val Gly Leu Val Pro Gln Gly Gly Leu Glu Thr Ser
```

<210> SEQ ID NO 23
<211> LENGTH: 13
<212> TYPE: PRT
<213> ORGANISM: Artificial
<220> FEATURE:
<223> OTHER INFORMATION: Synthetic Construct

<400> SEQUENCE: 23

Gly Leu Val Pro Gln Gly Gly Leu Glu Thr Ser Gln Pro
1               5                   10

<210> SEQ ID NO 24
<211> LENGTH: 15
<212> TYPE: PRT
<213> ORGANISM: Artificial
<220> FEATURE:
<223> OTHER INFORMATION: Synthetic Construct

<400> SEQUENCE: 24

Val Pro Gln Gly Gly Leu Glu Thr Ser Gln Pro Glu Gly Glu Ala
1               5                   10                  15

<210> SEQ ID NO 25
<211> LENGTH: 15
<212> TYPE: PRT
<213> ORGANISM: Artificial
<220> FEATURE:
<223> OTHER INFORMATION: Synthetic Construct

<400> SEQUENCE: 25

Gly Leu Glu Thr Ser Gln Pro Glu Gly Glu Ala Gly Val Gly Val
1               5                   10                  15

<210> SEQ ID NO 26
<211> LENGTH: 15
<212> TYPE: PRT
<213> ORGANISM: Artificial
<220> FEATURE:
<223> OTHER INFORMATION: Synthetic Construct

<400> SEQUENCE: 26

Ser Gln Pro Glu Gly Glu Ala Gly Val Gly Val Glu Ser Asn Ser
1               5                   10                  15

<210> SEQ ID NO 27
<211> LENGTH: 15
<212> TYPE: PRT
<213> ORGANISM: Artificial
<220> FEATURE:
<223> OTHER INFORMATION: Synthetic Construct

<400> SEQUENCE: 27

Gly Glu Ala Gly Val Gly Val Glu Ser Asn Ser Asp Gly Ala Ser
1               5                   10                  15

<210> SEQ ID NO 28
<211> LENGTH: 15
<212> TYPE: PRT
<213> ORGANISM: Artificial
<220> FEATURE:
<223> OTHER INFORMATION: Synthetic Construct

<400> SEQUENCE: 28

Val Gly Val Glu Ser Asn Ser Asp Gly Ala Ser Pro Glu Pro Cys
1               5                   10                  15

```
<210> SEQ ID NO 29
<211> LENGTH: 15
<212> TYPE: PRT
<213> ORGANISM: Artificial
<220> FEATURE:
<223> OTHER INFORMATION: Synthetic Construct

<400> SEQUENCE: 29

Ser Asn Ser Asp Gly Ala Ser Pro Glu Pro Cys Thr Val Thr Pro
1               5                   10                  15

<210> SEQ ID NO 30
<211> LENGTH: 15
<212> TYPE: PRT
<213> ORGANISM: Artificial
<220> FEATURE:
<223> OTHER INFORMATION: Synthetic Construct

<400> SEQUENCE: 30

Gly Ala Ser Pro Glu Pro Cys Thr Val Thr Pro Gly Ala Val Lys
1               5                   10                  15

<210> SEQ ID NO 31
<211> LENGTH: 14
<212> TYPE: PRT
<213> ORGANISM: Artificial
<220> FEATURE:
<223> OTHER INFORMATION: Synthetic Construct

<400> SEQUENCE: 31

Glu Pro Cys Thr Val Thr Pro Gly Ala Val Lys Leu Glu Lys
1               5                   10

<210> SEQ ID NO 32
<211> LENGTH: 14
<212> TYPE: PRT
<213> ORGANISM: Artificial
<220> FEATURE:
<223> OTHER INFORMATION: Synthetic Construct

<400> SEQUENCE: 32

Thr Val Thr Pro Gly Ala Val Lys Leu Glu Lys Glu Lys Leu
1               5                   10

<210> SEQ ID NO 33
<211> LENGTH: 15
<212> TYPE: PRT
<213> ORGANISM: Artificial
<220> FEATURE:
<223> OTHER INFORMATION: Synthetic Construct

<400> SEQUENCE: 33

Pro Gly Ala Val Lys Leu Glu Lys Glu Lys Leu Glu Gln Asn Pro
1               5                   10                  15

<210> SEQ ID NO 34
<211> LENGTH: 14
<212> TYPE: PRT
<213> ORGANISM: Artificial
<220> FEATURE:
<223> OTHER INFORMATION: Synthetic Construct

<400> SEQUENCE: 34

Lys Leu Glu Lys Glu Lys Leu Glu Gln Asn Pro Glu Glu Ser
1               5                   10
```

```
<210> SEQ ID NO 35
<211> LENGTH: 15
<212> TYPE: PRT
<213> ORGANISM: Artificial
<220> FEATURE:
<223> OTHER INFORMATION: Synthetic Construct

<400> SEQUENCE: 35

Lys Glu Lys Leu Glu Gln Asn Pro Glu Glu Ser Gln Asp Ile Lys
1               5                   10                  15

<210> SEQ ID NO 36
<211> LENGTH: 15
<212> TYPE: PRT
<213> ORGANISM: Artificial
<220> FEATURE:
<223> OTHER INFORMATION: Synthetic Construct

<400> SEQUENCE: 36

Glu Gln Asn Pro Glu Glu Ser Gln Asp Ile Lys Ala Leu Gln Lys
1               5                   10                  15

<210> SEQ ID NO 37
<211> LENGTH: 13
<212> TYPE: PRT
<213> ORGANISM: Artificial
<220> FEATURE:
<223> OTHER INFORMATION: Synthetic Construct

<400> SEQUENCE: 37

Glu Glu Ser Gln Asp Ile Lys Ala Leu Gln Lys Glu Leu
1               5                   10

<210> SEQ ID NO 38
<211> LENGTH: 15
<212> TYPE: PRT
<213> ORGANISM: Artificial
<220> FEATURE:
<223> OTHER INFORMATION: Synthetic Construct

<400> SEQUENCE: 38

Ser Gln Asp Ile Lys Ala Leu Gln Lys Glu Leu Glu Gln Phe Ala
1               5                   10                  15

<210> SEQ ID NO 39
<211> LENGTH: 15
<212> TYPE: PRT
<213> ORGANISM: Artificial
<220> FEATURE:
<223> OTHER INFORMATION: Synthetic Construct

<400> SEQUENCE: 39

Lys Ala Leu Gln Lys Glu Leu Glu Gln Phe Ala Lys Leu Leu Lys
1               5                   10                  15

<210> SEQ ID NO 40
<211> LENGTH: 15
<212> TYPE: PRT
<213> ORGANISM: Artificial
<220> FEATURE:
<223> OTHER INFORMATION: Synthetic Construct

<400> SEQUENCE: 40

Lys Glu Leu Glu Gln Phe Ala Lys Leu Leu Lys Gln Lys Arg Ile
1               5                   10                  15
```

<210> SEQ ID NO 41
<211> LENGTH: 14
<212> TYPE: PRT
<213> ORGANISM: Artificial
<220> FEATURE:
<223> OTHER INFORMATION: Synthetic Construct

<400> SEQUENCE: 41

Glu Gln Phe Ala Lys Leu Leu Lys Gln Lys Arg Ile Thr Leu
1               5                   10

<210> SEQ ID NO 42
<211> LENGTH: 14
<212> TYPE: PRT
<213> ORGANISM: Artificial
<220> FEATURE:
<223> OTHER INFORMATION: Synthetic Construct

<400> SEQUENCE: 42

Ala Lys Leu Leu Lys Gln Lys Arg Ile Thr Leu Gly Tyr Thr
1               5                   10

<210> SEQ ID NO 43
<211> LENGTH: 15
<212> TYPE: PRT
<213> ORGANISM: Artificial
<220> FEATURE:
<223> OTHER INFORMATION: Synthetic Construct

<400> SEQUENCE: 43

Leu Lys Gln Lys Arg Ile Thr Leu Gly Tyr Thr Gln Ala Asp Val
1               5                   10                  15

<210> SEQ ID NO 44
<211> LENGTH: 15
<212> TYPE: PRT
<213> ORGANISM: Artificial
<220> FEATURE:
<223> OTHER INFORMATION: Synthetic Construct

<400> SEQUENCE: 44

Arg Ile Thr Leu Gly Tyr Thr Gln Ala Asp Val Gly Leu Thr Leu
1               5                   10                  15

<210> SEQ ID NO 45
<211> LENGTH: 15
<212> TYPE: PRT
<213> ORGANISM: Artificial
<220> FEATURE:
<223> OTHER INFORMATION: Synthetic Construct

<400> SEQUENCE: 45

Gly Tyr Thr Gln Ala Asp Val Gly Leu Thr Leu Gly Val Leu Phe
1               5                   10                  15

<210> SEQ ID NO 46
<211> LENGTH: 15
<212> TYPE: PRT
<213> ORGANISM: Artificial
<220> FEATURE:
<223> OTHER INFORMATION: Synthetic Construct

<400> SEQUENCE: 46

Ala Asp Val Gly Leu Thr Leu Gly Val Leu Phe Gly Lys Val Phe
1               5                   10                  15

<210> SEQ ID NO 47

<211> LENGTH: 15
<212> TYPE: PRT
<213> ORGANISM: Artificial
<220> FEATURE:
<223> OTHER INFORMATION: Synthetic Construct

<400> SEQUENCE: 47

```
Leu Thr Leu Gly Val Leu Phe Gly Lys Val Phe Ser Gln Thr Thr
1               5                   10                  15
```

<210> SEQ ID NO 48
<211> LENGTH: 15
<212> TYPE: PRT
<213> ORGANISM: Artificial
<220> FEATURE:
<223> OTHER INFORMATION: Synthetic Construct

<400> SEQUENCE: 48

```
Val Leu Phe Gly Lys Val Phe Ser Gln Thr Thr Ile Cys Arg Phe
1               5                   10                  15
```

<210> SEQ ID NO 49
<211> LENGTH: 14
<212> TYPE: PRT
<213> ORGANISM: Artificial
<220> FEATURE:
<223> OTHER INFORMATION: Synthetic Construct

<400> SEQUENCE: 49

```
Lys Val Phe Ser Gln Thr Thr Ile Cys Arg Phe Glu Ala Leu
1               5                   10
```

<210> SEQ ID NO 50
<211> LENGTH: 15
<212> TYPE: PRT
<213> ORGANISM: Artificial
<220> FEATURE:
<223> OTHER INFORMATION: Synthetic Construct

<400> SEQUENCE: 50

```
Ser Gln Thr Thr Ile Cys Arg Phe Glu Ala Leu Gln Leu Ser Phe
1               5                   10                  15
```

<210> SEQ ID NO 51
<211> LENGTH: 15
<212> TYPE: PRT
<213> ORGANISM: Artificial
<220> FEATURE:
<223> OTHER INFORMATION: Synthetic Construct

<400> SEQUENCE: 51

```
Ile Cys Arg Phe Glu Ala Leu Gln Leu Ser Phe Lys Asn Met Cys
1               5                   10                  15
```

<210> SEQ ID NO 52
<211> LENGTH: 15
<212> TYPE: PRT
<213> ORGANISM: Artificial
<220> FEATURE:
<223> OTHER INFORMATION: Synthetic Construct

<400> SEQUENCE: 52

```
Glu Ala Leu Gln Leu Ser Phe Lys Asn Met Cys Lys Leu Arg Pro
1               5                   10                  15
```

<210> SEQ ID NO 53
<211> LENGTH: 15

```
<212> TYPE: PRT
<213> ORGANISM: Artificial
<220> FEATURE:
<223> OTHER INFORMATION: Synthetic Construct

<400> SEQUENCE: 53

Leu Ser Phe Lys Asn Met Cys Lys Leu Arg Pro Leu Leu Gln Lys
1               5                   10                  15

<210> SEQ ID NO 54
<211> LENGTH: 13
<212> TYPE: PRT
<213> ORGANISM: Artificial
<220> FEATURE:
<223> OTHER INFORMATION: Synthetic Construct

<400> SEQUENCE: 54

Asn Met Cys Lys Leu Arg Pro Leu Leu Gln Lys Trp Val
1               5                   10

<210> SEQ ID NO 55
<211> LENGTH: 14
<212> TYPE: PRT
<213> ORGANISM: Artificial
<220> FEATURE:
<223> OTHER INFORMATION: Synthetic Construct

<400> SEQUENCE: 55

Cys Lys Leu Arg Pro Leu Leu Gln Lys Trp Val Glu Glu Ala
1               5                   10

<210> SEQ ID NO 56
<211> LENGTH: 17
<212> TYPE: PRT
<213> ORGANISM: Artificial
<220> FEATURE:
<223> OTHER INFORMATION: Synthetic Construct

<400> SEQUENCE: 56

Arg Pro Leu Leu Gln Lys Trp Val Glu Glu Ala Asp Asn Asn Glu Asn
1               5                   10                  15

Leu

<210> SEQ ID NO 57
<211> LENGTH: 15
<212> TYPE: PRT
<213> ORGANISM: Artificial
<220> FEATURE:
<223> OTHER INFORMATION: Synthetic Construct

<400> SEQUENCE: 57

Trp Val Glu Glu Ala Asp Asn Asn Glu Asn Leu Gln Glu Ile Cys
1               5                   10                  15

<210> SEQ ID NO 58
<211> LENGTH: 15
<212> TYPE: PRT
<213> ORGANISM: Artificial
<220> FEATURE:
<223> OTHER INFORMATION: Synthetic Construct

<400> SEQUENCE: 58

Ala Asp Asn Asn Glu Asn Leu Gln Glu Ile Cys Lys Ala Glu Thr
1               5                   10                  15

<210> SEQ ID NO 59
```

```
<211> LENGTH: 15
<212> TYPE: PRT
<213> ORGANISM: Artificial
<220> FEATURE:
<223> OTHER INFORMATION: Synthetic Construct

<400> SEQUENCE: 59

Glu Asn Leu Gln Glu Ile Cys Lys Ala Glu Thr Leu Val Gln Ala
1               5                   10                  15

<210> SEQ ID NO 60
<211> LENGTH: 15
<212> TYPE: PRT
<213> ORGANISM: Artificial
<220> FEATURE:
<223> OTHER INFORMATION: Synthetic Construct

<400> SEQUENCE: 60

Glu Ile Cys Lys Ala Glu Thr Leu Val Gln Ala Arg Lys Arg Lys
1               5                   10                  15

<210> SEQ ID NO 61
<211> LENGTH: 15
<212> TYPE: PRT
<213> ORGANISM: Artificial
<220> FEATURE:
<223> OTHER INFORMATION: Synthetic Construct

<400> SEQUENCE: 61

Ala Glu Thr Leu Val Gln Ala Arg Lys Arg Lys Arg Thr Ser Ile
1               5                   10                  15

<210> SEQ ID NO 62
<211> LENGTH: 15
<212> TYPE: PRT
<213> ORGANISM: Artificial
<220> FEATURE:
<223> OTHER INFORMATION: Synthetic Construct

<400> SEQUENCE: 62

Val Gln Ala Arg Lys Arg Lys Arg Thr Ser Ile Glu Asn Arg Val
1               5                   10                  15

<210> SEQ ID NO 63
<211> LENGTH: 15
<212> TYPE: PRT
<213> ORGANISM: Artificial
<220> FEATURE:
<223> OTHER INFORMATION: Synthetic Construct

<400> SEQUENCE: 63

Lys Arg Lys Arg Thr Ser Ile Glu Asn Arg Val Arg Gly Asn Leu
1               5                   10                  15

<210> SEQ ID NO 64
<211> LENGTH: 15
<212> TYPE: PRT
<213> ORGANISM: Artificial
<220> FEATURE:
<223> OTHER INFORMATION: Synthetic Construct

<400> SEQUENCE: 64

Thr Ser Ile Glu Asn Arg Val Arg Gly Asn Leu Glu Asn Leu Phe
1               5                   10                  15

<210> SEQ ID NO 65
<211> LENGTH: 15
```

```
<212> TYPE: PRT
<213> ORGANISM: Artificial
<220> FEATURE:
<223> OTHER INFORMATION: Synthetic Construct

<400> SEQUENCE: 65

Asn Arg Val Arg Gly Asn Leu Glu Asn Leu Phe Leu Gln Cys Pro
1               5                   10                  15

<210> SEQ ID NO 66
<211> LENGTH: 15
<212> TYPE: PRT
<213> ORGANISM: Artificial
<220> FEATURE:
<223> OTHER INFORMATION: Synthetic Construct

<400> SEQUENCE: 66

Gly Asn Leu Glu Asn Leu Phe Leu Gln Cys Pro Lys Pro Thr Leu
1               5                   10                  15

<210> SEQ ID NO 67
<211> LENGTH: 15
<212> TYPE: PRT
<213> ORGANISM: Artificial
<220> FEATURE:
<223> OTHER INFORMATION: Synthetic Construct

<400> SEQUENCE: 67

Asn Leu Phe Leu Gln Cys Pro Lys Pro Thr Leu Gln Gln Ile Ser
1               5                   10                  15

<210> SEQ ID NO 68
<211> LENGTH: 15
<212> TYPE: PRT
<213> ORGANISM: Artificial
<220> FEATURE:
<223> OTHER INFORMATION: Synthetic Construct

<400> SEQUENCE: 68

Leu Gln Cys Pro Lys Pro Thr Leu Gln Gln Ile Ser His Ile Ala
1               5                   10                  15

<210> SEQ ID NO 69
<211> LENGTH: 14
<212> TYPE: PRT
<213> ORGANISM: Artificial
<220> FEATURE:
<223> OTHER INFORMATION: Synthetic Construct

<400> SEQUENCE: 69

Lys Pro Thr Leu Gln Gln Ile Ser His Ile Ala Gln Gln Leu
1               5                   10

<210> SEQ ID NO 70
<211> LENGTH: 15
<212> TYPE: PRT
<213> ORGANISM: Artificial
<220> FEATURE:
<223> OTHER INFORMATION: Synthetic Construct

<400> SEQUENCE: 70

Leu Gln Gln Ile Ser His Ile Ala Gln Gln Leu Gly Leu Glu Lys
1               5                   10                  15

<210> SEQ ID NO 71
<211> LENGTH: 15
<212> TYPE: PRT
```

```
<213> ORGANISM: Artificial
<220> FEATURE:
<223> OTHER INFORMATION: Synthetic Construct

<400> SEQUENCE: 71

Ser His Ile Ala Gln Gln Leu Gly Leu Glu Lys Asp Val Val Arg
1               5                   10                  15

<210> SEQ ID NO 72
<211> LENGTH: 15
<212> TYPE: PRT
<213> ORGANISM: Artificial
<220> FEATURE:
<223> OTHER INFORMATION: Synthetic Construct

<400> SEQUENCE: 72

Ala Gln Gln Leu Gly Leu Glu Lys Asp Val Val Arg Val Trp Phe
1               5                   10                  15

<210> SEQ ID NO 73
<211> LENGTH: 15
<212> TYPE: PRT
<213> ORGANISM: Artificial
<220> FEATURE:
<223> OTHER INFORMATION: Synthetic Construct

<400> SEQUENCE: 73

Gly Leu Glu Lys Asp Val Val Arg Val Trp Phe Cys Asn Arg Arg
1               5                   10                  15

<210> SEQ ID NO 74
<211> LENGTH: 15
<212> TYPE: PRT
<213> ORGANISM: Artificial
<220> FEATURE:
<223> OTHER INFORMATION: Synthetic Construct

<400> SEQUENCE: 74

Asp Val Val Arg Val Trp Phe Cys Asn Arg Arg Gln Lys Gly Lys
1               5                   10                  15

<210> SEQ ID NO 75
<211> LENGTH: 15
<212> TYPE: PRT
<213> ORGANISM: Artificial
<220> FEATURE:
<223> OTHER INFORMATION: Synthetic Construct

<400> SEQUENCE: 75

Val Trp Phe Cys Asn Arg Arg Gln Lys Gly Lys Arg Ser Ser Ser
1               5                   10                  15

<210> SEQ ID NO 76
<211> LENGTH: 14
<212> TYPE: PRT
<213> ORGANISM: Artificial
<220> FEATURE:
<223> OTHER INFORMATION: Synthetic Construct

<400> SEQUENCE: 76

Asn Arg Arg Gln Lys Gly Lys Arg Ser Ser Ser Asp Tyr Ala
1               5                   10

<210> SEQ ID NO 77
<211> LENGTH: 14
<212> TYPE: PRT
<213> ORGANISM: Artificial
```

```
<220> FEATURE:
<223> OTHER INFORMATION: Synthetic Construct

<400> SEQUENCE: 77

Arg Gln Lys Gly Lys Arg Ser Ser Asp Tyr Ala Gln Arg
1               5                   10

<210> SEQ ID NO 78
<211> LENGTH: 14
<212> TYPE: PRT
<213> ORGANISM: Artificial
<220> FEATURE:
<223> OTHER INFORMATION: Synthetic Construct

<400> SEQUENCE: 78

Gly Lys Arg Ser Ser Asp Tyr Ala Gln Arg Glu Asp Phe
1               5                   10

<210> SEQ ID NO 79
<211> LENGTH: 14
<212> TYPE: PRT
<213> ORGANISM: Artificial
<220> FEATURE:
<223> OTHER INFORMATION: Synthetic Construct

<400> SEQUENCE: 79

Ser Ser Ser Asp Tyr Ala Gln Arg Glu Asp Phe Glu Ala Ala
1               5                   10

<210> SEQ ID NO 80
<211> LENGTH: 15
<212> TYPE: PRT
<213> ORGANISM: Artificial
<220> FEATURE:
<223> OTHER INFORMATION: Synthetic Construct

<400> SEQUENCE: 80

Asp Tyr Ala Gln Arg Glu Asp Phe Glu Ala Ala Gly Ser Pro Phe
1               5                   10                  15

<210> SEQ ID NO 81
<211> LENGTH: 15
<212> TYPE: PRT
<213> ORGANISM: Artificial
<220> FEATURE:
<223> OTHER INFORMATION: Synthetic Construct

<400> SEQUENCE: 81

Arg Glu Asp Phe Glu Ala Ala Gly Ser Pro Phe Ser Gly Gly Pro
1               5                   10                  15

<210> SEQ ID NO 82
<211> LENGTH: 15
<212> TYPE: PRT
<213> ORGANISM: Artificial
<220> FEATURE:
<223> OTHER INFORMATION: Synthetic Construct

<400> SEQUENCE: 82

Glu Ala Ala Gly Ser Pro Phe Ser Gly Gly Pro Val Ser Phe Pro
1               5                   10                  15

<210> SEQ ID NO 83
<211> LENGTH: 14
<212> TYPE: PRT
<213> ORGANISM: Artificial
<220> FEATURE:
```

```
<223> OTHER INFORMATION: Synthetic Construct

<400> SEQUENCE: 83

Ser Pro Phe Ser Gly Gly Pro Val Ser Phe Pro Leu Ala Pro
1               5                   10

<210> SEQ ID NO 84
<211> LENGTH: 15
<212> TYPE: PRT
<213> ORGANISM: Artificial
<220> FEATURE:
<223> OTHER INFORMATION: Synthetic Construct

<400> SEQUENCE: 84

Ser Gly Gly Pro Val Ser Phe Pro Leu Ala Pro Gly Pro His Phe
1               5                   10                  15

<210> SEQ ID NO 85
<211> LENGTH: 14
<212> TYPE: PRT
<213> ORGANISM: Artificial
<220> FEATURE:
<223> OTHER INFORMATION: Synthetic Construct

<400> SEQUENCE: 85

Val Ser Phe Pro Leu Ala Pro Gly Pro His Phe Gly Thr Pro
1               5                   10

<210> SEQ ID NO 86
<211> LENGTH: 15
<212> TYPE: PRT
<213> ORGANISM: Artificial
<220> FEATURE:
<223> OTHER INFORMATION: Synthetic Construct

<400> SEQUENCE: 86

Pro Leu Ala Pro Gly Pro His Phe Gly Thr Pro Gly Tyr Gly Ser
1               5                   10                  15

<210> SEQ ID NO 87
<211> LENGTH: 15
<212> TYPE: PRT
<213> ORGANISM: Artificial
<220> FEATURE:
<223> OTHER INFORMATION: Synthetic Construct

<400> SEQUENCE: 87

Gly Pro His Phe Gly Thr Pro Gly Tyr Gly Ser Pro His Phe Thr
1               5                   10                  15

<210> SEQ ID NO 88
<211> LENGTH: 15
<212> TYPE: PRT
<213> ORGANISM: Artificial
<220> FEATURE:
<223> OTHER INFORMATION: Synthetic Construct

<400> SEQUENCE: 88

Gly Thr Pro Gly Tyr Gly Ser Pro His Phe Thr Ala Leu Tyr Ser
1               5                   10                  15

<210> SEQ ID NO 89
<211> LENGTH: 15
<212> TYPE: PRT
<213> ORGANISM: Artificial
<220> FEATURE:
<223> OTHER INFORMATION: Synthetic Construct
```

<400> SEQUENCE: 89

Tyr Gly Ser Pro His Phe Thr Ala Leu Tyr Ser Ser Val Pro Phe
1               5                   10                  15

<210> SEQ ID NO 90
<211> LENGTH: 12
<212> TYPE: PRT
<213> ORGANISM: Artificial
<220> FEATURE:
<223> OTHER INFORMATION: Synthetic Construct

<400> SEQUENCE: 90

His Phe Thr Ala Leu Tyr Ser Ser Val Pro Phe Pro
1               5                   10

<210> SEQ ID NO 91
<211> LENGTH: 15
<212> TYPE: PRT
<213> ORGANISM: Artificial
<220> FEATURE:
<223> OTHER INFORMATION: Synthetic Construct

<400> SEQUENCE: 91

Phe Thr Ala Leu Tyr Ser Ser Val Pro Phe Pro Glu Gly Glu Ala
1               5                   10                  15

<210> SEQ ID NO 92
<211> LENGTH: 15
<212> TYPE: PRT
<213> ORGANISM: Artificial
<220> FEATURE:
<223> OTHER INFORMATION: Synthetic Construct

<400> SEQUENCE: 92

Tyr Ser Ser Val Pro Phe Pro Glu Gly Glu Ala Phe Pro Pro Val
1               5                   10                  15

<210> SEQ ID NO 93
<211> LENGTH: 15
<212> TYPE: PRT
<213> ORGANISM: Artificial
<220> FEATURE:
<223> OTHER INFORMATION: Synthetic Construct

<400> SEQUENCE: 93

Pro Phe Pro Glu Gly Glu Ala Phe Pro Pro Val Ser Val Thr Thr
1               5                   10                  15

<210> SEQ ID NO 94
<211> LENGTH: 15
<212> TYPE: PRT
<213> ORGANISM: Artificial
<220> FEATURE:
<223> OTHER INFORMATION: Synthetic Construct

<400> SEQUENCE: 94

Gly Glu Ala Phe Pro Pro Val Ser Val Thr Thr Leu Gly Ser Pro
1               5                   10                  15

<210> SEQ ID NO 95
<211> LENGTH: 15
<212> TYPE: PRT

```
<213> ORGANISM: Artificial
<220> FEATURE:
<223> OTHER INFORMATION: Synthetic Construct

<400> SEQUENCE: 95

Pro Pro Val Ser Val Thr Thr Leu Gly Ser Pro Met His Ser Asn
1               5                   10                  15
```

IMMUNOGENIC EPITOPES AS TARGETS FOR UNIVERSAL CANCER VACCINES

CROSS-REFERENCE TO RELATED APPLICATIONS

This application is the U.S. national phase application filed under 35 U.S.C. §371 claiming benefit to International Patent Application No. PCT/US2010/049823, filed on Sep. 22, 2010, which is entitled to priority under 35 U.S.C. §119(e) to U.S. Provisional Patent Application No. 61/277,285, filed on Sep. 22, 2009, each of which application is hereby incorporated herein by reference in its entirety.

STATEMENT REGARDING FEDERALLY SPONSORED RESEARCH OR DEVELOPMENT

This invention was made with government support under CA135110, CA106802, AI054375 and CA109465, awarded by the National Institutes of Health. The U.S. Government therefore has certain rights in this invention.

BACKGROUND OF THE INVENTION

Recent studies have shown that the expression of limited set of genes is sufficient to induce pluripotency in adult cells (Takahashi et al., 2007 Cell 131: 861-872; Yamanaka, 2009 Cell 137: 13-17). Pathways that regulate stemness in embryonal stem (ES) cells or induced pluripotent stem (IPS) cells also bear striking resemblance to those in cancer (Utikal et al., 2009 Nature 460: 1145-1148; Krizhanovsky et al., 2009 Nature 460: 1085-1086; Wang et al., 2008 Cell 2: 297-299). Subsets of tumor cells expressing genes associated with pluripotency in ES cells have been implicated in the clonogenicity of human tumors and activation of ES-associated genes correlates with adverse outcome in several tumors (Ben-Porath et al., 2008 Nat Genet 40: 499-507; Glinsky 2008 J Clin Oncol 26: 2846-2853; Schoenhals et al., 2009 Biochem Biophys Res Common 383: 157-162). Both ES and IPS cells have considerable promise toward regenerative medicine (Yamanaka, 2009 Cell 137: 13-17). However, immunogenicity and tumorigenicity of these cells represent major potential challenges for effective translation of these approaches in the clinic (Yamanaka, 2009 Cell 137: 13-17, Knoepfler, 2009 Stem Cells 27: 1050-1056; Lui et al., 2009 Curr Stem Cell Res Ther 4: 70-80).

OCT4 forms part of the core transcriptional network of human ES cells and regulates the induction of pluripotency in adult cells (Boyer et al., 2005 Cell 122: 947-956). The capacity of the human immune system to recognize this critical stem-cell gene is not known, but has potential implications for the emerging clinical applications involving therapeutics with ES/IPS-derived cells, or immune-based targeting of stem-cell pathways in cancers, and in particular germ-cell tumors (GCTs).

BRIEF SUMMARY OF THE INVENTION

The present invention provides a composition comprising a molecule having a sequence derived from OCT4. Preferably, the composition induces peptide reactive T cells when cultured in the presence of peripheral blood mononuclear cells (PBMCs).

In one embodiment, the molecule is at least 90% identity with an amino acid sequence selected from the group consisting of SEQ ID NOs: 1 through 95 and any combination thereof.

In one embodiment, the molecule has a nucleic acid sequence encoding an amino acid sequence selected from the group consisting of SEQ ID NOs: 1 through 95 and any combination thereof.

In one embodiment, the molecule is at least 90% identity with an amino acid sequence selected from the group consisting of SEQ ID NOs: 53 through 77 and any combination thereof.

In one embodiment, the molecule has a nucleic acid sequence encoding an amino acid sequence selected from the group consisting of SEQ ID NOs: 53 through 77 and any combination thereof.

In one embodiment, the molecule is at least 90% identity with an amino acid sequence selected from the group consisting of SEQ ID NOs: 53, 54, 55, 60, 61, 62, 63, 65, 67, 70, 71, 72, 73, 74, 75, 76, 77, and any combination thereof.

In one embodiment, the molecule has a nucleic acid sequence encoding an amino acid sequence selected from the group consisting of SEQ ID NOs: 53, 54, 55, 60, 61, 62, 63, 65, 67, 70, 71, 72, 73, 74, 75, 76, 77, and any combination thereof.

The invention also provides an OCT4 specific cell, wherein the cell has been contacted with a composition comprising a molecule having a sequence derived from OCT4, wherein the composition induces peptide reactive T cells when cultured in the presence of PBMCs.

In one embodiment, the cells is an antigen presenting cell.
In one embodiment, the cell is a T cell.

The invention provides a method of activating a cell comprising contacting the cell with the composition comprising a molecule having a sequence derived from OCT4, wherein the composition induces peptide reactive T cells when cultured in the presence of PBMCs.

In one embodiment, the cell is an antigen presenting cell.
In one embodiment, the cell is a T cell.

The invention also provides a vaccine for inhibiting proliferation of cells expressing OCT4. The vaccine comprises a composition comprising a molecule having a sequence derived from OCT4, wherein the composition induces peptide reactive T cells when cultured in the presence of PBMCs.

In one embodiment, the cells expressing OCT4 are cancer cells.

In one embodiment, the cells expressing OCT4 are stem cells.

The present invention provides a method of treating or preventing a disease or condition associated with overexpression of OCT 4 in a mammal. The method comprises administering to a mammal in need thereof a vaccine comprising a composition comprising a molecule having a sequence derived from OCT4, wherein the composition induces peptide reactive T cells when cultured in the presence of PBMCs.

In one embodiment, the disease or condition associated with overexpression of OCT4 is cancer.

In one embodiment, the disease or condition associated with overexpression of OCT4 is a result of stem cell based therapy in the mammal.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIGS. 1A through 1D, is a series of images depicting immunity to OCT4 in freshly isolated PBMCs from healthy blood donors. FIGS. 1A and 1B are images depicting reactivity of freshly isolated human PBMCs from healthy donors to OCT4 peptide library: $2 \times 10^5$ PBMCs were cultured alone or in the presence of 3 μg/mL of OCT4 peptide mixes, or PHA, as a control. After 48 h, the culture supernatant was harvested and analyzed for the presence of IP10 by Luminex assay. FIG. 1A is an image depicting data for representative healthy donors with or without detectable reactivity to OCT4 peptide library. FIG. 1B is an image depicting data for reactivity to the positive OCT4 mix (represented as fold-change in reactive mix compared with control) in all 30 donors tested. Based on interassay and intra-assay variance, ≥2-fold increase in IP10 production (in reactive mix versus control), with a minimal absolute measurement of 100 pg/mL, was predetermined to be positive for the presence of antigen-specific T cells. FIG. 1C is an image depicting bulk PBMCs or those depleted of CD3+ T cells were cultured alone (control) or with OCT4 peptide library. After 48 h, the culture supernatant was harvested and analyzed for the presence of IP10 by Luminex assay. Data are representative of similar experiments on three donors. FIG. 1D is an image depicting PBMCs that were cultured alone or OCT4 peptide mix in the presence of either anti-IFN-γ blocking antibody or isotype control antibody. After 48 h, the culture supernatant was harvested and analyzed for the presence of IP10 by Luminex assay. Data are representative of similar experiments on three donors.

FIGS. 2A and 2B, is a series of images depicting antigen dependent proliferation of OCT4-specific memory T cells. FIG. 2A is an image depicting proliferative response to OCT4 peptide library: $2 \times 10^5$ PBMCs were labeled with carboxyfluorescein diacetate succinimidyl ester (CFSE) and cultured with 1 μg/mL of anti-CD28 and anti-CD49d antibody alone (control) or in the presence of OCT4-derived peptides (3 μg/mL). (Left) Proliferation of CD3$^+$-gated cells in a representative donor. Note the predominant proliferation of CD4+ T cells. (Right) Antigen-dependent proliferation in six donors with or without reactivity in the IP10 assay, as in FIG. 1A. FIG. 2B is an image depicting PBMCs depleted of CD45RO+ T cells using immunomagnetic beads (or left undepleted) before stimulation with OCT4 peptides (Left), or PHA as a control (Right).

FIGS. 3A and 3B, is a series of images depicting fine specificity of OCT4-specific T-cell immunity and activation of peptide-specific T cells. FIG. 3A is an image depicting reactivity to individual peptides: PBMCs were cultured with individual peptides from submix 3 to determine the specific reactive peptide. After 48 h, culture supernatant was harvested and analyzed for the presence of IP10 by Luminex assay. The figure shows the reactivity against individual peptides for 10 healthy donors. FIG. 3B is an image depicting expansion of peptide-reactive T cells with peptide-pulsed DCs. Monocyte-derived mature DCs loaded with active peptide (as identified in experiments in FIG. 2A) were used to stimulate autologous T cells. The presence of peptide-specific IFNγ-producing T cells was analyzed by intracellular cytokine flow cytometry following restimulation with anti-CD28 and anti-CD49d, with or without stimulating peptide. Data shown are representative of four different donors.

FIGS. 4A and 4B, depicts immunity to OCT4 in patients with GCTs. FIG. 4A is an image depicting reactivity of freshly isolated human PBMCs from newly diagnosed GCT patients (n=21) or healthy controls (n=30) to OCT4 peptide library (as in FIG. 1B) or PHA as a control. Positive reactivity was predetermined to be ≥2-fold increase in IP10 production (in reactive mix versus control), with a minimal absolute measurement of 100 pg/mL. FIG. 4B is an image depicting the effect of antitumor therapy on OCT4 immunity: PBMCs from GCT patients (n=12) were analyzed at baseline and at the completion of therapy for reactivity to OCT4 and to viral antigens (CEF) as a control. Data shown are reactivity at baseline and at the completion of therapy. Bold lines represent mean reactivity.

DETAILED DESCRIPTION OF THE INVENTION

Figure 1:
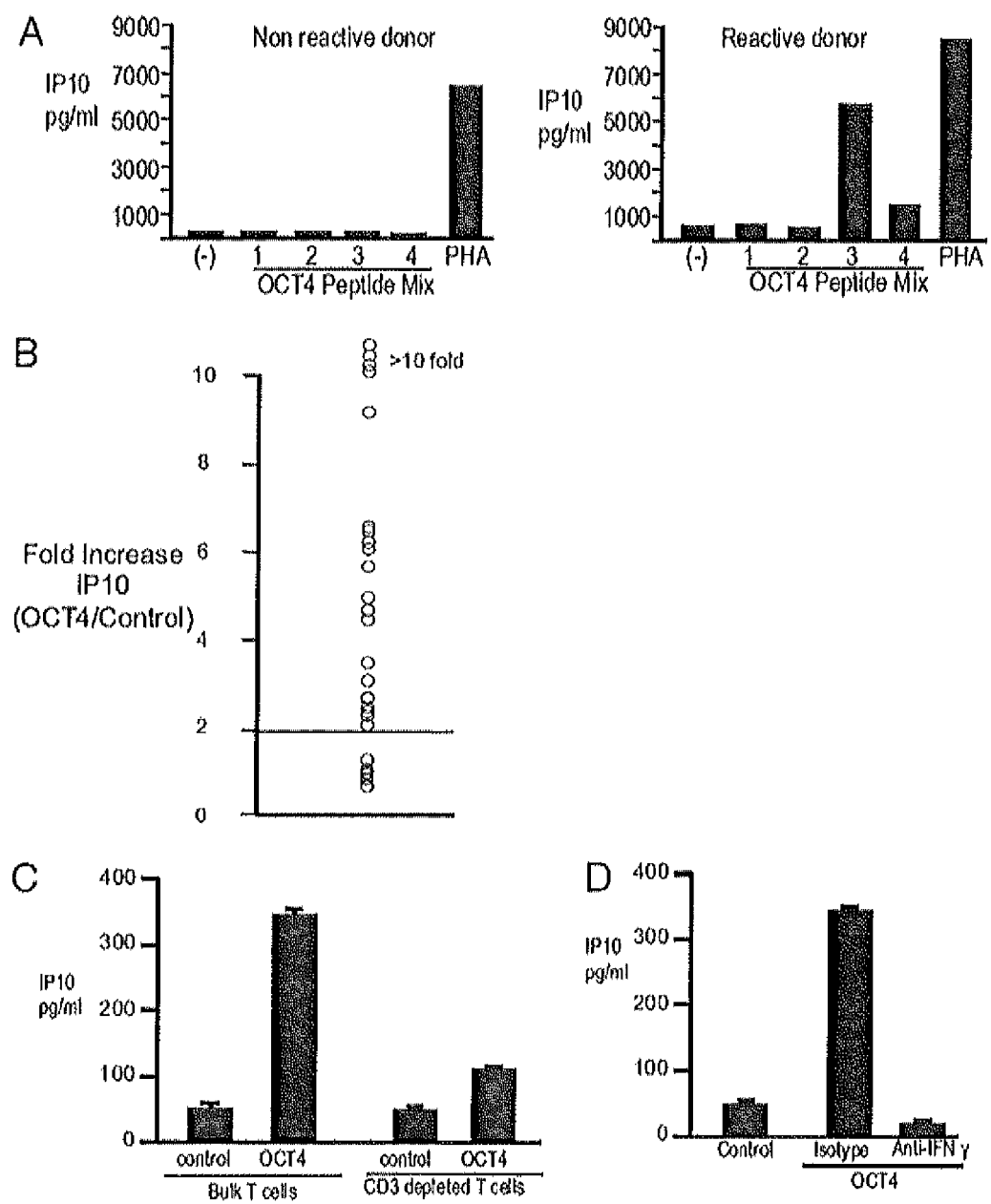
FIG. 1, comprising

The present invention is based on the discovery that most healthy humans harbor OCT4-specific memory T cells that are readily detectable in freshly isolated peripheral blood mononuclear cells (PBMCs) and that an OCT4-specific response was detected in patients undergoing curative therapy for germ-cell tumors (GCTs). Thus, a functional OCT4-specific immune response is needed to treat a disease associated with over-expression of OCT4.

Accordingly, the invention encompasses OCT4 as a marker for detection of cancer in a human subject. In another embodiment, the invention provides a method of targeting OCT4 for the development of immunotherapeutic compounds and methods.

Thus, the invention provides an immunological composition comprising an epitope of OCT4 useful in eliciting an immune response. A composition comprising epitopes of OCT4 not only is useful as a prophylactic therapeutic agent for initial protection, but is also useful as a therapeutic agent for treatment of an ongoing condition associated with unregulated expression of OCT4 in the subject.

The present invention also provides methods for treating or preventing a condition associated with the over-expression of OCT4, e.g. cancer. The present invention also provides methods for treating or preventing a condition associated with tumorgenicity relating to stem cell based therapies. Such methods involve the step of administering to a subject in need thereof an OCT4 peptide or combinations of peptides of the invention. Administration of such peptide(s) results in the induction of anti-tumor immunity. Thus, the present invention provides methods for inducing anti-tumor immunity in a subject, such methods involving the step of administering to the subject the OCT4 peptide or combinations of peptides of the invention, as well as pharmaceutical compositions for treating or preventing a conditions associated with the over-expression of OCT4.

The invention encompasses a method for inducing a T cell response to OCT4 in a mammal. The method comprises administering an antigen presenting cell (APC) that specifically induces proliferation of a T cell specific for OCT4. Once sufficient numbers of antigen-specific T cells are obtained using the APC to expand the T cell, the antigen-specific T cells so obtained are administered to the mammal, thereby inducing a T cell response to the OCT4 in the mammal. This is because the data disclosed herein amply demonstrate that antigen-specific T cells can be readily produced by stimulating resting T cells using the APC of the invention.

Definitions

As used herein, each of the following terms has the meaning associated with it in this section.

The articles "a" and "an" are used herein to refer to one or to more than one (i.e. to at least one) of the grammatical object of the article. By way of example, "an element" means one element or more than one element.

The term "about" will be understood by persons of ordinary skill in the art and will vary to some extent depending on the context in which it is used. As used herein, "about" is meant to encompass variations of ±20% or ±10%, more preferably ±5%, even more preferably ±1%, and still more preferably ±0.1%.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

As used herein, to "alleviate" a disease means reducing the severity of one or more symptoms of the disease.

The term "antibody" as used herein, refers to an immunoglobulin molecule, which is able to specifically bind to a specific epitope on an antigen. Antibodies can be intact immunoglobulins derived from natural sources or from recombinant sources and can be immunoactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies (Harlow et al., 1988; Houston et al., 1988; Bird et al., 1988).

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded soley by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

"An antigen presenting cell" (APC) is a cell that are capable of activating T cells, and includes, but is not limited to, monocytes/macrophages, B cells and dendritic cells (DCs).

The term "dendritic cell" or "DC" refers to any member of a diverse population of morphologically similar cell types found in lymphoid or non-lymphoid tissues. These cells are characterized by their distinctive morphology, high levels of surface MHC-class II expression. DCs can be isolated from a number of tissue sources. DCs have a high capacity for sensitizing MHC-restricted T cells and are very effective at presenting antigens to T cells in situ. The antigens may be self-antigens that are expressed during T cell development and tolerance, and foreign antigens that are present during normal immune processes.

As used herein, an "activated DC" is a DC that has been contacted with a peptide or combination of peptides of the invention. The activated DC is capable of activating an immune cell.

The term "mature DC" as used herein, is defined as a dendritic cell that expresses high levels of MHC class II, CD80 (B7.1) and CD86 (B7.2) molecules. In contrast, immature dendritic cells express low levels of MHC class II, CD80 (B7.1) and CD86 (B7.2) molecules but have a great capacity to take up an antigen.

"Antigen-loaded APC" or an "antigen-pulsed APC" includes an APC, which has been exposed to an antigen and activated by the antigen. For example, an APC may become Ag-loaded in vitro, e.g., during culture in the presence of an antigen. The APC may also be loaded in vivo by exposure to an antigen.

An "antigen-loaded APC" is traditionally prepared in one of two ways: (1) small peptide fragments, known as antigenic peptides, are "pulsed" directly onto the outside of the APCs; or (2) the APC is incubated with whole proteins or protein particles which are then ingested by the APC. These proteins are digested into small peptide fragments by the APC and are eventually transported to and presented on the APC surface. In addition, the antigen-loaded APC can also be generated by introducing a polynucleotide encoding an antigen into the cell.

The term "anti-tumor effect" as used herein, refers to a biological effect which can be manifested by a decrease in tumor volume, a decrease in the number of tumor cells, a decrease in the number of metastases, an increase in life expectancy, or amelioration of various physiological symptoms associated with the cancerous condition. An "anti-tumor effect" can also be manifested by the ability of the peptides, polynucleotides, cells and antibodies of the invention in prevention of the occurrence of tumor in the first place.

The term "B-cell" as used herein is defined as a cell derived from the bone marrow and/or spleen. B cells can develop into plasma cells which produce antibodies.

The term "cancer" as used herein is defined as disease characterized by the rapid and uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer, germ-cell tumors, and the like.

A "disease" is a state of health of an animal wherein the animal cannot maintain homeostasis, and wherein if the disease is not ameliorated, then the animal's health continues to deteriorate.

The terms "neoplasia," "hyperplasia," and "tumor" are often commonly referred to as "cancer," which is a general name for more than 100 disease that are characterized by uncontrolled, abnormal growth of cells. Examples of malignancies include but are not limited to acute lymphoblastic leukemia; acute myeloid leukemia; adrenocortical carcinoma; AIDS-related lymphoma; cancer of the bile duct; bladder cancer, bone cancer, osteosarcomal malignant fibrous histiocytomal brain stem gliomal brain tumor; breast cancer, bronchial adenomas; carcinoid tumors; adrenocortical carcinoma; central nervous system lymphoma; cancer of the sinus, cancer of the gall bladder; gastric cancer; cancer of the salivary glands; cancer of the esophagus; neural cell cancer; intestinal cancer (e.g., of the large or small intestine); cervical cancer; colon cancer, colorectal cancer; cutaneous T-cell lymphoma; B-cell lymphoma; T-cell lymphoma; endometrial cancer; epithelial cancer; endometrial cancer; intraocular melanoma; retinoblastoma; hairy cell leukemia; liver cancer; Hodgkin's disease; Kaposi's sarcoma; acute lymphoblastic leukemia; lung cancer; non-Hodgkin's lymphoma; melanoma; multiple myeloma; neuroblastoma; prostate cancer; retinoblastoma; Ewing's sarcoma; vaginal cancer; Waldenstrom's macroglobulinemia; adenocarcinomas; ovarian cancer, chronic lymphocytic leukemia, pancreatic cancer, germ-cell tumors and Wilm's tumor.

The term "DNA" as used herein is defined as deoxyribonucleic acid.

By the term "effective amount", as used herein, is meant an amount that when administered to a mammal, causes a detectable level of immune response compared to the immune response detected in the absence of the composition. Immune response can be readily assessed by a plethora of art-recognized methods. The skilled artisan would understand that the amount of the compound or composition administered herein varies and can be readily determined based on a number of factors such as the disease or condition being treated, the age and health and physical condition of the mammal being treated, the severity of the disease, the particular compound being administered, and the like.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

The term "epitope" as used herein is defined as a small chemical molecule on an antigen that can elicit an immune response, inducing B and/or T cell responses. An antigen can have one or more epitopes. Most antigens have many epitopes; i.e., they are multivalent. In general, an epitope is roughly five amino acids and/or sugars in size. One skilled in the art understands that generally the overall three-dimensional structure, rather than the specific linear sequence of the molecule, is the main criterion of antigenic specificity and therefore distinguishes one epitope from another.

The term "helper Tcell" as used herein is defined as an effector T cell whose primary function is to promote the activation and functions of other B and T lymphocytes and or macrophages. Most helper T cells are CD4 T-cells.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are completely or 100% homologous at that position. The percent homology between two sequences is a direct function of the number of matching or homologous positions, e.g., if half (e.g., five positions in a polymer ten subunits in length) of the positions in two compound sequences are homologous then the two sequences are 50% identical, if 90% of the positions, e.g., 9 of 10, are matched or homologous, the two sequences share 90% homology. By way of example, the DNA sequences 5'ATTGCC3' and 5TATGGC3' share 50% homology.

In addition, when the terms "homology" or "identity" are used herein to refer to the nucleic acids and proteins, it should be construed to be applied to homology or identity at both the nucleic acid and the amino acid sequence levels.

The term "biomarker" or "marker" is a characteristic that is objectively measured and evaluated as an indicator of normal biological processes, pathological processes, or pharmacological responses to a therapeutic intervention. The biomarker can for example describe a substance whose detection indicates a particular disease state. The biomarker may be a peptide that causes disease or is associated with susceptibility to disease. In some instances, the biomarker may be a gene that causes disease or is associated with susceptibility to disease. In any event, the biomarker can be differentially present (i.e., increased or decreased) in a biological sample from a subject or a group of subjects having a first phenotype (e.g., having a disease) as compared to a biological sample from a subject or group of subjects having a second phenotype (e.g., not having the disease). A biomarker may be differentially present at any level, but is generally present at a level that is increased by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, by at least 100%, by at least 110%, by at least 120%, by at least 130%, by at least 140%, by at least 150%, or more; or is generally present at a level that is decreased by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, or by 100% (i.e., absent). A biomarker is preferably differentially present at a level that is statistically significant (i.e., a p-value less than 0.05 and/or a q-value of less than 0.10 as determined using either Welch's T-test or Wilcoxon's rank-sum Test).

As used herein, "immunogen" refers to a substance that is able to stimulate or induce a humoral antibody and/or cell-mediated immune response in a mammal.

"Mammal" as used herein preferably means "human."

By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region.

"Proliferation" is used herein to refer to the reproduction or multiplication of similar forms of entities, for example proliferation of a cell. That is, proliferation encompasses production of a greater number of cells, and can be measured by, among other things, simply counting the numbers of cells, measuring incorporation of $^3$H-thymidine into the cell, and the like.

"Patient" for the purposes of the present invention includes humans and other animals, particularly mammals, and other organisms. Thus the methods are applicable to both human therapy and veterinary applications. In a preferred embodiment the patient is a mammal, and in a most preferred embodiment the patient is human.

As used herein, the term "pharmaceutically acceptable carrier" means a chemical composition with which the active ingredient may be combined and which, following the combination, can be used to administer the active ingredient to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

The term "self-antigen" as used herein is defined as an antigen that is expressed by a host cell or tissue. Self-antigens may be tumor antigens, but in certain embodiments, are expressed in both normal and tumor cells. A skilled artisan would readily understand that a self-antigen may be overexpressed in a cell.

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some embodiments, the cells are culture in vitro. In other embodiments, the cells are not cultured in vitro.

As used herein, the term "subject" is to be understood as referring to any animal. However, preferably, the subject is a mammal and, more preferably a human.

The term "T-cell" as used herein is defined as a thymus-derived cell that participates in a variety of cell-mediated immune reactions.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

A "therapeutic" treatment is a treatment administered to a patient who exhibits signs of pathology for the purpose of diminishing or eliminating those signs and/or decreasing or diminishing the frequency, duration and intensity of the signs.

"Therapeutically effective amount" is an amount of a compound of the invention, that when administered to a patient, ameliorates a symptom of the disease. The amount of a compound of the invention which constitutes a "therapeutically effective amount" will vary depending on the compound, the disease state and its severity, the age of the patient to be treated, and the like. The therapeutically effective amount can be determined routinely by one of ordinary skill in the art having regard to his own knowledge and to this disclosure.

The term "vaccine" as used herein is defined as a material used to provoke an immune response after administration of the material to a mammal. In some instances, a "vaccine" is a composition, a peptide, protein or a nucleic acid encoding a peptide or combination of peptides of the invention, which serves to protect an animal against a disease and/or to treat an animal already affected compared with an otherwise identical animal to which the vaccine is not administered or compared with the animal prior to the administration of the vaccine.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range and, when appropriate, partial integers of the numerical values within ranges. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The invention relates to the discovery that T cells responding to a peptide epitope or combination of peptide epitopes derived from OCT4 can be readily detected and expanded in culture using a peptide-loaded dendritic cell. Thus, the present invention provides a peptide or combinations of peptides, polynucleotides and pharmaceutical and vaccine compositions including same which are useful in modulation of immune responses, in inhibition of tumor growth, both primary tumor and metastases, in treatment of cancer by way of prevention and cure.

The invention provides an immunological composition comprising a peptide epitope or combination of peptide epitopes derived from OCT4 useful in eliciting an immune response. The composition comprising one or more peptides of the invention not only are useful as a prophylactic therapeutic agent for initial protection, but is also useful as a therapeutic agent for treatment of an ongoing condition associated with unregulated expression of OCT4 in the subject.

The invention also provides an immunological composition comprising one or more peptides of OCT4 useful in activating and expanding T cells.

The immunogenic compositions of the present invention may also include nucleic acids encoding one or more of the immunogenic peptides disclosed herein.

Compositions

The present invention provides peptides, for example peptides number 1-95 (SEQ ID NOs: 1-95), alone or in various combinations, that when administered to a mammal, elicit an anti-OCT4 immune response, including activating OCT4 specific T cells. Further, when the peptide or combination of peptides are inoculated into a mammal, it elicits an immune response which serves to protect the inoculated mammal against conditions associated with unregulated expression of OCT4 including, but are not limited to cancer and tumorgenicity relating to stem cell based therapies.

As exemplified herein, the peptide or combinations of peptides of the invention can be obtained in large quantities for use as a vaccine. The peptide or combinations of peptides of the invention are also useful as a diagnostic reagent for assessing the presence or absence of an anti-OCT4 immune response in a mammal. Such an assessment is made by obtaining serum or cells from the mammal and reacting it with the peptide or combinations of peptides of the invention in a standard assay known in the art for detecting binding to the peptide.

In one embodiment, the present invention provides compositions that are useful as immunomodulatory agents, for example, in stimulating immune responses and in tumor growth inhibition. Thus, these compositions are useful for the treatment of cancer and autoimmune diseases. In some instances, the compositions are useful in treating conditions associated with tumorgenicity relating to stem cell based therapies.

In one embodiment, the peptide or combinations of peptides of the invention are immunomodulatory. The peptide or combinations of peptides of the invention of the invention may serve as an immunostimulatory agent to elicit an anti-tumor activity or may serve as an agent for immunotherapy or as an immune-stimulator against unregulated cellular proliferation associated with stem cell based therapies. As an immunomodulator, the peptide or combinations of peptides of the invention can induce shifts in the immune system from undesirable responses to beneficial responses.

In one embodiment, the invention provides a composition comprising one or more of the peptides listed in Table 1 (peptide numbers 1-95 which correspond to SEQ ID NOs: 1-95, respectively). In one embodiment, the composition of the invention comprises one or more peptides selected from peptide number 53-77 which correspond to SEQ ID NOs: 53-77, respectively.

In yet another embodiment, the invention provides a composition comprising one or more of the peptides listed in Table 1 (peptide numbers 1-95 which correspond to SEQ ID NOs: 1-95, respectively). In one embodiment, the composition of the invention comprises one or more peptides selected from peptide number 53-77 which correspond to SEQ ID NOs: 53-77, respectively.

In yet another embodiment, the composition of the invention comprises a peptide selected from the group consisting of peptide number 53, 54, 55, 60, 61, 62, 63, 65, 67, 70, 71, 72, 73, 74, 75, 76, 77, and any combinations thereof. That is, peptide numbers 53, 54, 55, 60, 61, 62, 63, 65, 67, 70, 71, 72, 73, 74, 75, 76, 77, and any combination there represent a non-limiting example of peptides tested that exhibited hot-spots of promiscuous reactivity within the OCT4 protein. These hot-spots represent exemplary conserved domains within the OCT4 protein that can be used to design an immunogenic composition against OCT 4.

In one embodiment, the invention provides a peptide, or a fragment of a peptide, a homolog, a variant, a derivative or a salt of a peptide having the sequence of any one or more of SEQ ID NOs 1 through 95, wherein the biological activity of the peptide or fragment thereof is retained. In yet another embodiment, the invention provides a fragment of a peptide, a homolog, a variant, a derivative or a salt of a peptide having the sequence of any one or more of SEQ ID NOs 53 through 77, wherein the biological activity of the peptide or fragment is retained. In yet another embodiment, the invention provides a fragment of a peptide, a homolog, a variant, a derivative or a salt of a peptide having the sequence of any one or more of SEQ ID NOs 53, 54, 55, 60, 61, 62, 63, 65, 67, 70, 71, 72, 73, 74, 75, 76, 77, wherein the biological activity of the peptide or fragment is retained.

The invention should also be construed to include any form of a peptide having substantial homology to the peptides disclosed herein. Preferably, a peptide which is "substantially homologous" is about 50% homologous, more preferably about 70% homologous, even more preferably about 80% homologous, more preferably about 90% homologous, even more preferably, about 95% homologous, and even more preferably about 99% homologous to amino acid sequence of the peptides disclosed herein.

According to yet another embodiment, the peptide or combination of peptides of the present invention are capable of generating an OCT4-specific immune response. In another embodiment, the peptide or combination of peptides of the present invention are capable of generating OCT4-specific T cells. For example, the OCT4-specific T cell is able to respond to a peptide epitope or combination of peptide epitopes derived from OCT4. Can you define what this cell is?

Furthermore, in another embodiment, the present invention provides a peptide useful for inhibiting tumor growth, wherein the peptide is selected from the group consisting of a peptide, a fragment of a peptide, a homolog, a variant, a derivative or a salt of a peptide having the sequence of any one or more of SEQ ID NOs 1 through 95, wherein the biological activity of the peptide or fragment is retained. In another embodiment, the present invention provides a peptide useful for inhibiting tumor growth selected from a peptide, a fragment of a peptide, a homolog, a variant, a derivative or a salt of a peptide having the sequence of any one or more of SEQ ID NOs 53 through 77, wherein the biological activity of the peptide or fragment is retained. In another embodiment, the present invention provides a peptide useful for inhibiting tumor growth selected from a peptide, a fragment of a peptide, a homolog, a variant, a derivative or a salt of a peptide having the sequence of any one or more of SEQ ID NOs 53, 54, 55, 60, 61, 62, 63, 65, 67, 70, 71, 72, 73, 74, 75, 76, 77, wherein the biological activity of the peptide or fragment is retained.

Furthermore, in another embodiment, the present invention provides a peptide useful for inducing an immune response against tumor cells, wherein the peptide is selected from the group consisting a peptide, a fragment of a peptide, a homolog, a variant, a derivative or a salt of a peptide having the sequence of any one or more of SEQ ID NOs 1 through 95, wherein the biological activity of the peptide or fragment is retained. In another embodiment, the present invention provides a peptide useful for inducing an immune response against tumor cells selected from a peptide, a fragment of a peptide, a homolog, a variant, a derivative or a salt of a peptide having the sequence of any one or more of SEQ ID NOs 53 through 77, wherein the biological activity of the peptide or fragment is retained. In another embodiment, the present invention provides a peptide useful for inducing an immune response against tumor cells selected from a peptide, a fragment of a peptide, a homolog, a variant, a derivative or a salt of a peptide having the sequence of any one or more of SEQ ID NOs 53, 54, 55, 60, 61, 62, 63, 65, 67, 70, 71, 72, 73, 74, 75, 76, 77, wherein the biological activity of the peptide or fragment is retained.

In another embodiment, the present invention provides a peptide useful for inducing an immune response against unregulated growth of stem cells wherein the peptide is selected from the group consisting of a peptide, a fragment of a peptide, a homolog, a variant, a derivative or a salt of a peptide having the sequence of any one or more of SEQ ID NOs 1 through 95, wherein the biological activity of the peptides or fragments is retained. In another embodiment, the present invention provides a peptide useful for inducing an immune response against unregulated growth of stem cells selected from a peptide, a fragment of a peptide, a homolog, a variant, a derivative or a salt of a peptide having the sequence of any one or more of SEQ ID NOs 53 through 77, wherein the biological activity of the peptides or fragments is retained. In another embodiment, the present invention provides a peptide useful for inducing an immune response against unregulated growth of stem cells wherein the peptide is selected from the group consisting of a peptide, a fragment of a peptide, a homolog, a variant, a derivative or a salt of a peptide having the sequence of any one or more of SEQ ID NOs 53, 54, 55, 60, 61, 62, 63, 65, 67, 70, 71, 72, 73, 74, 75, 76, 77, wherein the biological activity of the peptides or fragments is retained.

Peptides of the present invention can be prepared using well known techniques. For example, the peptides can be prepared synthetically, using either recombinant DNA technology or chemical synthesis. Peptides of the present invention may be synthesized individually or as longer polypeptides composed of two or more peptides. The peptides of the present invention are preferably isolated, i.e., substantially free of other naturally occurring host cell proteins and fragments thereof.

The peptides of the present invention may contain modifications, such as glycosylation, side chain oxidation, or phosphorylation; so long as the modifications do not destroy the biological activity of the peptides. Other modifications include incorporation of D-amino acids or other amino acid mimetics that can be used, for example, to increase the serum half life of the peptides.

The peptides of the invention can be modified whereby the amino acid is substituted for a different amino acid in which the properties of the amino acid side-chain are conserved (a process known as conservative amino acid substitution). Examples of properties of amino acid side chains are hydrophobic amino acids (A, I, L, M, F, P, W, Y, V), hydrophilic amino acids (R, D, N, C, E, Q, G, H, K, S, T), and side chains having the following functional groups or characteristics in common: an aliphatic side-chain (G, A, V, L, I, P); a hydroxyl group containing side-chain (S, T, Y); a sulfur atom containing side-chain (C, M); a carboxylic acid and amide containing side-chain (D, N, E, Q); a base containing side-chain (R, K, H); and an aromatic containing side-chain (H, F, Y, W). Note, the parenthetic letters indicate the one-letter codes of amino acids.

The peptides of the invention can be prepared as a combination, which includes two or more of peptides of the invention, for use as a vaccine for a disease associated with the over-expression of OCT4, e.g. cancers, or a condition associated with unregulated cell proliferation following stem cell based therapy. The peptides may be in a cocktail or may be conjugated to each other using standard techniques. For example, the peptides can be expressed as a single polypeptide sequence. The peptides in the combination may be the same or different.

The present invention should also be construed to encompass "mutants," "derivatives," and "variants" of the peptides of the invention (or of the DNA encoding the same) which mutants, derivatives and variants are peptides which are altered in one or more amino acids (or, when referring to the nucleotide sequence encoding the same, are altered in one or more base pairs) such that the resulting peptide (or DNA) is not identical to the sequences recited herein, but has the same biological property as the peptides disclosed herein.

The invention also provides a polynucleotide encoding at least one peptide selected from a peptide having the sequence of any one or more of SEQ ID NOs 1 through 95. The nucleic acid sequences include both the DNA sequence that is transcribed into RNA and the RNA sequence that is translated into a peptide. According to other embodiments, the polynucleotides of the invention are inferred from the amino acid sequence of the peptides of the invention. As is known in the art several alternative polynucleotides are possible due to redundant codons, while retaining the biological activity of the translated peptides.

Further, the invention encompasses an isolated nucleic acid encoding a peptide having substantial homology to the peptides disclosed herein. Preferably, the nucleotide sequence of an isolated nucleic acid encoding a peptide of the invention is "substantially homologous", that is, is about 60% homologous, more preferably about 70% homologous, even more preferably about 80% homologous, more preferably about 90% homologous, even more preferably, about 95% homologous, and even more preferably about 99% homologous to a nucleotide sequence of an isolated nucleic acid encoding a peptide of the invention.

It is to be understood explicitly that the scope of the present invention encompasses homologs, analogs, variants, derivatives and salts, including shorter and longer peptides and polynucleotides, as well as peptide and polynucleotide analogs with one or more amino acid or nucleic acid substitution, as well as amino acid or nucleic acid derivatives, non-natural amino or nucleic acids and synthetic amino or nucleic acids as are known in the art, with the stipulation that these modifications must preserve the biological activity of the original molecule. Specifically any active fragments of the active peptides as well as extensions, conjugates and mixtures are included and are disclosed herein according to the principles of the present invention.

The invention should be construed to include any and all isolated nucleic acids which are homologous to the nucleic acids described and referenced herein, provided these homologous nucleic acids encode peptides having the biological activity of the peptides disclosed herein.

The skilled artisan would understand that the nucleic acids of the invention encompass an RNA or a DNA sequence encoding a peptide of the invention, and any modified forms thereof, including chemical modifications of the DNA or RNA which render the nucleotide sequence more stable when it is cell free or when it is associated with a cell. Chemical modifications of nucleotides may also be used to enhance the efficiency with which a nucleotide sequence is taken up by a cell or the efficiency with which it is expressed in a cell. Any and all combinations of modifications of the nucleotide sequences are contemplated in the present invention.

Further, any number of procedures may be used for the generation of mutant, derivative or variant forms of a protein of the invention using recombinant DNA methodology well known in the art such as, for example, that described in Sambrook and Russell, supra, and Ausubel et al., supra. Procedures for the introduction of amino acid changes in a peptide or polypeptide by altering the DNA sequence encoding the polypeptide are well known in the art and are also described in these, and other, treatises.

Thus the invention includes an isolated nucleic acid encoding one or more of peptides having a sequence selected from the group consisting of SEQ ID NOs: 1 through 95, preferably peptides having a sequence selected from the group consisting of SEQ ID NOs: 53 through 75, more preferably peptides having a sequence selected from the group consisting of SEQ ID NOs: 53, 54, 55, 60, 61, 62, 63, 65, 67, 70, 71, 72, 73, 74, 75, 76, 77, and any combination thereof.

Vectors

The nucleic acids encoding the peptide or combinations of peptides of the invention of the invention can be incorporated into suitable vectors, including but not limited to, retroviral vectors. Such vectors are well known in the art and are therefore not described in detail herein. The nucleic acids or the vectors containing them usefully can be transferred into a desired cell, which cell is preferably derived from a patient. Advantageously, the invention provides an off-the-shelf composition allowing rapid modification of a patient's own cells (or those of another mammal) to rapidly and easily produce modified cells having excellent cancer cell killing properties.

In one embodiment, the invention includes a nucleic acid sequence encoding one or more peptides of the invention operably linked to a nucleic acid comprising a promoter/regulatory sequence such that the nucleic acid is preferably capable of directing expression of the protein encoded by the nucleic acid. Thus, the invention encompasses expression vectors and methods for the introduction of exogenous DNA into cells with concomitant expression of the exogenous DNA in the cells such as those described, for example, in Sambrook et al. (2001, Molecular Cloning: A Laboratory Manual, Cold Spring Harbor Laboratory, New York), and in Ausubel et al. (1997, Current Protocols in Molecular Biology, John Wiley & Sons, New York). The incorporation of a desired polynucleotide into a vector and the choice of vectors is well-known in the art as described in, for example, Sambrook et al., supra, and Ausubel et al., supra.

The polynucleotide can be cloned into a number of types of vectors. However, the present invention should not be construed to be limited to any particular vector. Instead, the present invention should be construed to encompass a wide plethora of vectors which are readily available and/or well-known in the art. For example, the polynucleotide of the invention can be cloned into a vector including, but not limited to a plasmid, a phagemid, a phage derivative, an animal virus, and a cosmid. Vectors of particular interest include expression vectors, replication vectors, probe generation vectors, and sequencing vectors.

In specific embodiments, the expression vector is selected from the group consisting of a viral vector, a bacterial vector and a mammalian cell vector. Numerous expression vector systems exist that comprise at least a part or all of the compositions discussed above. Prokaryote- and/or eukaryote-vector based systems can be employed for use with the present invention to produce polynucleotides, or their cognate polypeptides. Many such systems are commercially and widely available.

Further, the expression vector may be provided to a cell in the form of a viral vector. Viral vector technology is well known in the art and is described, for example, in Sambrook et al. (2001), and in Ausubel et al. (1997), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (See, e.g., WO 01/96584; WO 01/29058; and U.S. Pat. No. 6,326,193).

For expression of the desired nucleotide sequences of the invention, at least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 genes, a discrete element overlying the start site itself helps to fix the place of initiation.

Additional promoter elements, i.e., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either co-operatively or independently to activate transcription.

A promoter may be one naturally associated with a gene or polynucleotide sequence, as may be obtained by isolating the 5' non-coding sequences located upstream of the coding segment and/or exon. Such a promoter can be referred to as "endogenous." Similarly, an enhancer may be one naturally associated with a polynucleotide sequence, located either downstream or upstream of that sequence. Alternatively, certain advantages will be gained by positioning the coding polynucleotide segment under the control of a recombinant or heterologous promoter, which refers to a promoter that is not normally associated with a polynucleotide sequence in its natural environment. A recombinant or heterologous enhancer refers also to an enhancer not normally associated with a polynucleotide sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (U.S. Pat. No. 4,683,202, U.S. Pat. No. 5,928,906). Furthermore, it is contemplated the control sequences that direct transcription and/or expression of sequences within non-nuclear organdies such as mitochondria, chloroplasts, and the like, can be employed as well.

Naturally, it will be important to employ a promoter and/or enhancer that effectively directs the expression of the DNA segment in the cell type, organelle, and organism chosen for expression. Those of skill in the art of molecular biology generally know how to use promoters, enhancers, and cell type combinations for protein expression, for example, see Sambrook et al. (2001). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

A promoter sequence exemplified in the experimental examples presented herein is the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, Moloney virus promoter, the avian leukemia virus promoter, Epstein-Barr virus immediate early promoter, Rous sarcoma virus promoter, as well as human gene promoters such as, but not limited to, the actin promoter, the myosin promoter, the hemoglobin promoter, and the muscle creatine promoter. Further, the invention should not be limited to the use of constitutive promoters. Inducible promoters are also contemplated as part of the invention. The use of an inducible promoter in the invention provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter. Further, the invention includes the use of a tissue specific promoter, which promoter is active only in a desired tissue. Tissue specific promoters are well known in the art and include, but are not limited to, the HER-2 promoter and the PSA associated promoter sequences.

In order to assess the expression of the nucleotide sequences encoding the peptide or combinations of peptides of the invention, the expression vector to be introduced into a cell can also contain either a selectable marker gene or a reporter gene or both to facilitate identification and selection of expressing cells from the population of cells sought to be transfected or infected through viral vectors. In other embodiments, the selectable marker may be carried on a separate piece of DNA and used in a co-transfection procedure. Both selectable markers and reporter genes may be flanked with appropriate regulatory sequences to enable expression in the host cells. Useful selectable markers are known in the art and include, for example, antibiotic-resistance genes, such as neo and the like.

Reporter genes are used for identifying potentially transfected cells and for evaluating the functionality of regulatory sequences. Reporter genes that encode for easily assayable proteins are well known in the art. In general, a reporter gene is a gene that is not present in or expressed by the recipient organism or tissue and that encodes a protein whose expression is manifested by some easily detectable property, e.g., enzymatic activity. Expression of the reporter gene is assayed at a suitable time after the DNA has been introduced into the recipient cells.

Suitable reporter genes may include genes encoding luciferase, beta-galactosidase, chloramphenicol acetyl transferase, secreted alkaline phosphatase, or the green fluorescent protein gene (see, e.g., Ui-Tel et al., 2000 FEBS Lett. 479:79-82). Suitable expression systems are well known and may be prepared using well known techniques or obtained commercially. Internal deletion constructs may be generated using unique internal restriction sites or by partial digestion of non-unique restriction sites. Constructs may then be transfected into cells that display high levels of siRNA polynucleotide and/or polypeptide expression. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Antigen Presenting Cell Therapy

The present invention also provides methods of inducing antigen presenting cells (APCs) using one or more peptides of the invention. The APCs can be induced by inducing dendritic cells from the peripheral blood monocytes and then contacting (stimulating) them with one or more peptides of this invention in vitro, ex vivo or in vivo. When one or more peptides of the present invention are administered to the mammal in need thereof, APCs that have the peptide or combinations of peptides of the invention immobilized to them are induced in the body of the mammal. Alternatively, after immobilizing the peptide or combinations of peptides of the invention to the APCs, the cells can be administered to the subject as a vaccine. For example, the ex vivo administration may include the steps of: collecting APCs from a mammal, and contacting the APCs with one or more peptides of the present invention.

The invention also provides a method for inducing APCs having a high level of T cell inducibility, in which the method includes the step of transferring genes composed of polynucleotide(s) encoding one or more peptides of this invention to APCs cells in vitro. The introduced genes may be in the form of DNAs or RNAs. For the method of introduction, without particular limitations, various methods conventionally performed in this field, such as lipofection, electroporation, and calcium phosphate method may be suitably used. By transferring the gene into APCs, the gene undergoes transcription, translation, and such in the cell, and then the obtained protein is processed by MHC Class I or Class II, and proceeds through a presentation pathway to present partial peptides.

The present invention further provides methods for inducing OCT4-specific T cells using one or more peptides of the invention. When the peptide or combinations of peptides of the invention are administered to a subject, T cells are induced in the body of the subject, and the strength of the immune system targeting the cells expressing OCT4, e.g. cancer cells in the tumor tissues or tumorgenicity relating to stem cell based therapies is thereby enhanced.

Alternatively, the peptide or combinations of peptides of the invention may be used in the context of an ex vivo therapeutic method, in which subject-derived APC and desired T cells or peripheral blood mononuclear leukocytes are contacted (stimulated) with one or more peptides of this invention in vitro, and, after inducing T cell activation, the cells are returned to the subject. For example, the method may include the steps of: collecting APCs from a subject, contacting the APCs with a peptide or combinations of peptides of the invention, mixing the APCs with the desired T cell type and co-culturing so as to induce the T-cells, and collecting the T cells from the co-culture.

Alternatively, according to the present invention, use of the peptide or combinations of peptides of the invention for manufacturing a pharmaceutical composition inducing T cells is provided. Further, the present invention also provides the peptide or combinations of peptides of the invention for inducing the desired T cell type. The activated T cells can be administered to the subject as a vaccine.

The present invention further provides isolated T cells induced using the peptide or combinations of peptides of the invention. The T cells, induced by stimulation with an APC presenting one or more peptides of this invention, are preferably derived from subjects who are the target of treatment and/or prevention, and can be administered alone or in combination with other drugs, including one or more peptides of this having anti-tumor activity. The obtained T cells act specifically against target cells presenting the one or more peptides of this invention, or preferably the same peptide(s) used for induction. The target cells may be cells that express OCT4 endogenously, or cells that are transfected with OCT4. Cells that present the peptide or combinations of peptides of the invention on the cell surface, due to stimulation with these peptides, can also become targets of attack.

The present invention also provides APCs presenting complexes formed between HLA antigens and one or more peptides of this invention. The APCs, obtained through contact with the one or more peptides of this invention or the nucleotides encoding such peptides, are preferably derived from subjects who are the target of treatment and/or prevention, and can be administered as vaccines, alone or in combination with other drugs, including the peptides, or T cells of the present invention.

The present invention provides compositions and methods for stimulating APC, preferably dendritic cells (DCs), in the context of immunotherapy to stimulate the immune response in a mammal. DCs can be manipulated by stimulating them with a peptide or combination of peptides of the invention and causing the DCs to mature so that they stimulate anti-tumor immunity in a mammal in need thereof.

In one embodiment, the invention includes a method for inducing a T cell response to OCT4 in a mammal. The method comprises administering to the mammal an APC, such as a DC, wherein the APC has been activated by contacting the APC with a peptide or combination of peptides of the invention thereby generating a peptide-loaded APC.

In one embodiment, the invention relates to novel APCs produced and methods for their use to, inter alia, expand a desired T cell, to activate T cells, to expand specific T cell, as well as numerous therapeutic uses relating to expansion and stimulation of T cells using the peptide-load APC and peptide or combinations of peptides of the invention. In some instances, the OCT4 stimulated DCs can be used to expand OCT4-specific T cells.

The present invention relates to the discovery that a DC contacted with a peptide or combination of peptides of the invention can be used to induce expansion of peptide-specific T cells. A skilled artisan would recognize that the DCs contacted with the peptide or combinations of peptides of the invention of the invention are considered primed or otherwise peptide-loaded. The peptide-loaded DCs of the invention are useful for eliciting an immune response against OCT4. Accordingly, the peptide-load DCs of the invention can be used to treat a disease associated with unregulated expression of OCT4.

In on embodiment, the present invention encompasses methods and compositions for reducing and/or eliminating unregulated cellular proliferation associated with stem cell therapy.

The DCs of the invention can be generated by transducing the cells with a vector that results in expression of a peptide or combination of peptides of the invention. Any of a variety of methods well known to one of skill in the art can be used to transduce the DCs.

In the context of an expression vector, the vector can be readily introduced into a host cell, e.g., mammalian, bacterial, yeast or insect cell by any method in the art. For example, the expression vector can be transferred into a host cell by physical, chemical or biological means. It is readily understood that the introduction of the expression vector comprising the polynucleotide of the invention yields a silenced cell with respect to a cytokine signaling regulator.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York), and in Ausubel et al. (1997, Current Protocols in Molecular Biology, John Wiley & Sons, New York).

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus 1, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). The preparation and use of such systems is well known in the art.

Regardless of the method used to introduce exogenous nucleic acids into a host cell or otherwise expose a cell to the inhibitor of the present invention, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

The invention also includes generating a peptide-load DC by contacting or otherwise "pulsed" or "primed" with a peptide or combination of peptides of the invention. For example, the DC may become "peptide-loaded" in vitro, e.g., by culture ex vivo in the presence of a peptide or combination of peptides of the invention, or directly genetically modified to express the same, or in vivo by exposure to the peptide or combination of peptides of the invention.

A skilled artisan would also readily understand that the DC can be "pulsed" in a manner that exposes the DC to the peptide or combination of peptides for a time sufficient to promote presentation of that peptide or combination of peptides on the surface of the DC. For example, DCs can be exposed to a peptide directly onto the outside of the DC; or the DCs can be incubated with whole proteins or protein particles which are then ingested by the DCs. These whole proteins are digested into small peptide fragments by the DC and eventually carried to and presented on the DC surface. Antigen in peptide form may be exposed to the cell by standard "pulsing" techniques described herein. The antigen may also be mixed in nature being derived from tissue and cell extracts.

The present invention includes various methods for pulsing APCs including, but not limited to, loading APCs with whole antigen in the form of a protein, cDNA or mRNA. However, the invention should not be construed to be limited to the specific form of the antigen used for pulsing the APC. Rather, the invention encompasses other methods known in the art for generating an antigen loaded APC. Preferably, the APC is transfected with mRNA encoding a defined antigen. mRNA corresponding to a gene product whose sequence is known can be rapidly generated in vitro using appropriate primers and reverse transcriptase-polymerase chain reaction (RT-PCR) coupled with transcription reactions. Transfection of an APC with an mRNA provides an advantage over other antigen-loading techniques for generating a pulsed APC. For example, the ability to amplify RNA from a microscopic amount of tissue, i.e. tumor tissue, extends the use of the APC for vaccination to a large number of patients.

The peptide-loaded DC can be produced by exposure of the DC to the peptide or combination of peptides either in vitro or in vivo. In the case where the DC is pulsed in vitro, the DC is plated on a culture dish and exposed to the peptide or combination of peptides in a sufficient amount and for a sufficient period of time to allow the peptide or combination of peptides to bind to the DC. The amount and time necessary to achieve binding of the antigen to the DC may be determined by using methods known in the art or otherwise disclosed herein. Other methods known to those of skill in the art, for example immunoassays or binding assays, may be used to detect the presence of the peptide or combination of peptides on the DC following exposure to the peptides.

In a further embodiment of the invention, the DC may be genetically modified using a vector which allows for the expression of a specific peptide or combination of peptides by the DC. The protein which is expressed by the DC may then be processed and presented on the cell surface on an MHC receptor. The modified DC may then be used as an immunogenic composition to induce an immune response. In some instances, the modified DC can be used to culture expand T cells.

As discussed elsewhere herein, vectors may be prepared to include a specific polynucleotide which encodes and expresses a desired protein. Preferably, retroviral or lentiviral vectors are used to infect the cells. More preferably, adenoviral vectors are used to infect the cells.

As discussed elsewhere herein, various methods can be used for transfecting a polynucleotide into a host cell. The methods include, but are not limited to, calcium phosphate precipitation, lipofection, particle bombardment, microinjection, electroporation, colloidal dispersion systems (i.e. macromolecule complexes, nanocapsules, microspheres, beads, and lipid-based systems including oil-in-water emulsions, micelles, mixed micelles, and liposomes).

Various types of vectors and methods of introducing nucleic acids into a cell are discussed elsewhere herein. For example, a vector encoding an antigen may be introduced into a host cell by any method in the art. For example, the expression vector can be transferred into a host cell by physical, chemical or biological means. See, for example, Sambrook et al. (2001, Molecular Cloning: A Laboratory Manual, Cold Spring Harbor Laboratory, New York), and in Ausubel et al. (1997, Current Protocols in Molecular Biology, John Wiley & Sons, New York). It is readily understood that the introduction of the expression vector comprising a polynucleotide encoding an antigen yields a pulsed cell.

The invention includes a cellular composition comprising a DC that has been modified to enhance its ability to induce OCT4 specific immune response. In some instances, the cellular composition comprises a DC that has been modified to enhance its ability to culture expand T cells.

Accordingly, the invention includes a method for specifically expanding a T cell population subset. More particularly, the method comprises contacting a population of T cells comprising at least one T cell of a subset of interest with an APC capable of expanding that T cell. One skilled in the art would understand, based upon the disclosure provided herein, that T cell subsets include T helper ($T_{H1}$ and $T_{H2}$) CD4 expressing, cytotoxic T lymphocyte (CTL) (Tc1 or Tc2) T regulatory ($T_{REG}$), $T_{C/S}$, naïve, memory, central memory, effector memory, and γδT cells. Therefore, cell populations enriched for a particular T cell subset can be readily produced using the methods of the invention.

Vaccine

For an antigenic composition to be useful as a vaccine, the antigenic composition must induce an immune response to the antigen in a cell, tissue or mammal (e.g., a human). Preferably, the vaccine induces a protective immune response in the mammal. As used herein, an "immunological composition" may comprise an antigen (e.g., a peptide or polypeptide), a nucleic acid encoding an antigen (e.g., an antigen expression vector), a cell expressing or presenting an antigen or cellular component. In particular embodiments the antigenic composition comprises or encodes all or part of any peptide antigen described herein, or an immunologically functional equivalent thereof. In other embodiments, the antigenic composition is in a mixture that comprises an additional immunostimulatory agent or nucleic acids encoding such an agent. Immunostimulatory agents include but are not limited to an additional antigen, an immunomodulator, an antigen presenting cell or an adjuvant. In other embodiments, one or more of the additional agent(s) is covalently bonded to the antigen or an immunostimulatory agent, in any combination. In certain embodiments, the antigenic composition is conjugated to or comprises an HLA anchor motif amino acids.

In the context of the present invention, the term "vaccine" (also referred to as an immunogenic composition) refers to a substance that induces anti-tumor immunity or suppresses cancers upon inoculation into animals. In some instances, the vaccine of the invention can be used to inducing immunity to unregulated expression of OCT4 to regulate pluripotency-related pathways relating to tumorgenicity in the context of stem cell therapy.

A vaccine of the present invention may vary in its composition of nucleic acid and/or cellular components. In a non-limiting example, a nucleic encoding an antigen might also be formulated with an adjuvant. Of course, it will be understood that various compositions described herein may further comprise additional components. For example, one or more vaccine components may be comprised in a lipid or liposome. In another non-limiting example, a vaccine may comprise one or more adjuvants. A vaccine of the present invention, and its various components, may be prepared and/or administered by any method disclosed herein or as would be known to one of ordinary skill in the art, in light of the present disclosure.

In one embodiment, the peptide vaccine of the invention includes, but is not limited to a peptide mixed with adjuvant substances and a peptide which is introduced together with an APC. The most common cells used for the latter type of vaccine bone marrow and peripheral blood derived dendritic cells, as these cells express costimulatory molecules that help activation of T cells. WO00/06723 discloses a cellular vaccine composition which includes an APC presenting tumor associated antigen peptides. Presenting the peptide can be effected by loading the APC with a polynucleotide (e.g., DNA, RNA) encoding the peptide or loading the APC with the peptide itself.

Thus, the present invention also encompasses a method of inducing anti-tumor immunity using one or more of peptides having the amino acid sequence of SEQ ID NOs: 1 through 95 or a variant thereof (i.e., including 1, 2, or several (e.g., up to 5) amino acid substitutions, deletions, or additions). When a certain peptide or combination of peptides induce an anti-tumor immune response upon inoculation into an animal, the peptide or combination of peptides are decided to have anti-tumor immunity inducing effect. The induction of the anti-tumor immunity by a peptide or combination of peptides can be detected by observing in vivo or in vitro the response of the immune system in the host against the peptide.

For example, a method for detecting the induction of cytotoxic T lymphocytes is well known. A foreign substance that enters the living body is presented to T cells and B cells by the action of APCs. T cells that respond to the antigen presented by APC in an antigen specific manner differentiate into cytotoxic T cells (also referred to as cytotoxic T lymphocytes or CTLs) due to stimulation by the antigen. These antigen stimulated cells then proliferate. This process is referred to herein as "activation" of T cells. Therefore, CTL induction by a certain peptide or combination of peptides of the invention can be evaluated by presenting the peptide to a T cell by APC, and detecting the induction of CTL. Furthermore, APCs have the effect of activating CD4+ T cells, CD8+ T cells, macrophages, eosinophils and NK cells. Since CD4+ T cells are also important in anti-tumor immunity, the anti-tumor immunity inducing action of the peptide can be evaluated using the activation effect of these cells as indicators.

A method for evaluating the inducing action of CTL using dendritic cells (DCs) as APC is well known in the art. DC is a representative APC having the strongest CTL inducing action among APCs. In this method, the test peptide or combination of peptides are initially contacted with DC and then this DC is contacted with T cells. Detection of T cells having cytotoxic effects against the cells of interest after the contact with DC shows that the test peptide or combination of peptides have an activity of inducing the cytotoxic T cells. Activity of CTL against tumors can be detected, for example, using the lysis of $^{51}$Cr-labeled tumor cells as the indicator. Alternatively, it is well known to evaluate the degree of tumor cell damage using 3H-thymidine uptake activity or LDH (lactose dehydrogenase)-release as the indicator. Furthermore, it can be also examined by measuring IFN-gamma produced and released by CTL in the presence of antigen-presenting cells that carry immobilized peptide or combination of peptides by visualizing using anti-IFN-gamma antibodies, such as an ELISPOT assay.

Apart from DC, peripheral blood mononuclear cells (PBMCs) may also be used as the APC. The induction of CTL is reported to be enhanced by culturing PBMC in the presence of GM-CSF and IL-4. Similarly, CTL has been shown to be induced by culturing PBMC in the presence of keyhole limpet hemocyanin (KLH) and IL-7.

The test peptide or combination of peptides confirmed to possess CTL inducing activity by these methods are peptides having DC activation effect and subsequent CTL inducing activity. Therefore, a peptide or combination of peptides that induce CTL against cells expressed OCT4 are useful as vaccines against diseases associating OCT4, e.g. cancers. Furthermore, APC that have acquired the ability to induce CTL against a disease associated with the over-expression of OCT4, by contacting with the peptide or combination of peptides are useful as vaccines against the disease. Furthermore, CTL that have acquired cytotoxicity due to presentation of the peptide or combination of peptides by APC can be also used as vaccines against a disease associated with OCT4 expression.

Generally, when using a peptide for cellular immunotherapy, efficiency of the CTL-induction can be increased by combining a plurality of peptides having different structures and contacting them with DC. Therefore, when stimulating DC with protein fragments, it is advantageous to use a mixture of multiple types of fragments.

The induction of anti-tumor immunity by a peptide or combination of peptides can be further confirmed by observing the induction of antibody production against tumors. For example, when antibodies against a peptide or combination of peptides are induced in a laboratory animal immunized with the peptide or combination of peptides, and when growth, proliferation and/or metastasis of tumor cells is suppressed by those antibodies, the peptide or combination of peptides are determined to induce anti-tumor immunity.

The induction of anti-tumor immunity by a peptide or combination of peptides can be further confirmed by observing the activation of OCT4 specific T cells and the presence of peptide-specific IFNγ-secreting CD4+ T cells. For example, when peptide-specific IFNγ-secreting CD4+ T cells are induced in a laboratory animal immunized with the peptide or combination of peptides, and when growth, proliferation and/or metastasis of tumor cells is suppressed by those peptide-specific IFNγ-secreting CD4+ T cells, the peptide or combination of peptides are determined to induce anti-tumor immunity. In some instances, peptide-specific IFNγ-secreting CD4+ T cells are induced using peptide-loaded antigen presenting cells.

Anti-tumor immunity can be induced by administering a vaccine of this invention, and the induction of anti-tumor immunity enables treatment and prevention of a disease associated with the over-expression of OCT4. Therapy against or prevention of the onset of a disease associated with the over-expression of OCT4 may include inhibition of the growth of cells expressing OCT4, involution of these cells and suppression of occurrence of these cells. Decrease in mortality of individuals having a disease associating OCT4, decrease of the disease markers in the blood, alleviation of detectable symptoms accompanying the disease and such are also included in the therapy or prevention of the disease. Such therapeutic and preventive effects are preferably statistically significant, for example, observed at a significance level of 5% or less, wherein the therapeutic or preventive effect of a vaccine against a disease associated with unregulated expression of OCT4, is compared to a control without vaccine administration. For example, Student's West, the Mann-Whitney U-test or ANOVA may be used for determining statistical significance.

The invention provides a method for treating, or preventing a disease or condition associated with the unregulated expression of OCT4. The therapeutic compounds or compositions of the invention may be administered prophylactically or therapeutically to subjects suffering from or at risk of (or susceptible to) developing the disease or condition. Such subjects may be identified using standard clinical methods. In the context of the present invention, prophylactic administration occurs prior to the manifestation of overt clinical symptoms of disease, such that a disease or disorder is prevented or alternatively delayed in its progression. In the context of the field of medicine, the term "prevent" encompasses any activity which reduces the burden of mortality or morbidity from disease. Prevention can occur at primary, secondary and tertiary prevention levels. While primary prevention avoids the development of a disease, secondary and tertiary levels of prevention encompass activities aimed at preventing the progression of a disease and the emergence of symptoms as well as reducing the negative impact of an already established disease by restoring function and reducing disease-related complications.

In the context of cancer treatment, the term "efficacious" refers to a treatment that leads to a decrease in size, prevalence or metastatic potential of cancer in a subject. When a treatment is applied prophylactically, "efficacious" means that the treatment retards or prevents occurrence of cancer or alleviates a clinical symptom of cancer. The assessment of cancer can be made using standard clinical protocols. Furthermore, the efficaciousness of a treatment may be determined in association with any known method for diagnosing or treating cancer. For example, cancer can be diagnosed histopathologically or by identifying symptomatic anomalies.

The peptide or combination of peptides of the invention having immunological activity, or a polynucleotide or vector encoding such a peptide or combination of peptides, may be combined with an adjuvant. An adjuvant refers to a compound that enhances the immune response against the peptide or combination of peptides when administered together (or successively) with the peptide having immunological activity. Examples of suitable adjuvants include cholera toxin, salmonella toxin, alum and such, but are not limited thereto. Furthermore, a vaccine of this invention may be combined appropriately with a pharmaceutically acceptable carrier. Examples of such carriers are sterilized water, physiological saline, phosphate buffer, culture fluid and such. Furthermore, the vaccine may contain as necessary, stabilizers, suspensions, preservatives, surfactants and such. The vaccine is administered systemically or locally. Vaccine administration may be performed by single administration or boosted by multiple administrations.

When using cells of the invention (e.g., peptide-load antigen presenting cell or peptide-specific IFNγ-secreting CD4+ T cells) as the vaccine, a disease or condition associated with the unregulated expression of OCT4 can be treated or prevented, for example, by the ex vivo method. For example, PBMCs of the subject receiving treatment or prevention are collected, contacted ex vivo with a peptide or combination of peptides of the invention Following the induction of peptide-load antigen presenting cells or peptide-specific IFNγ-secreting CD4+ T cells, the cells may be administered to the subject. The cells of the invention can be induced by introducing a vector encoding the peptide or combination of peptides into them ex vivo. The cells induced in vitro can be cloned prior to administration. By cloning and growing cells having high activity of damaging target cells, cellular immunotherapy can be performed more effectively. Furthermore, cells of the invention isolated in this manner may be used for cellular immunotherapy not only against individuals from whom the cells are derived, but also against similar types of diseases in other individuals.

Dosage and Formulation (Pharmaceutical Compositions)

The present invention envisions treating a disease or condition associated with unregulated expression of OCT4 in a mammal by the administration of a therapeutic composition of the invention to a mammal in need thereof. Administration of the therapeutic composition in accordance with the present invention may be continuous or intermittent, depending, for example, upon the recipient's physiological condition, whether the purpose of the administration is therapeutic or prophylactic, and other factors known to skilled practitioners. The administration of the compositions of the invention may be essentially continuous over a preselected period of time or may be in a series of spaced doses. Both local and systemic administration is contemplated. The amount administered will vary depending on various factors including, but not limited to, the composition chosen, the particular disease, the weight, the physical condition, and the age of the mammal, and whether prevention or treatment is to be achieved. Such factors can be readily determined by the clinician employing animal models or other test systems which are well known to the art One or more suitable unit dosage forms having the therapeutic agent(s) of the invention, which, as discussed below, may optionally be formulated for sustained release (for example using microencapsulation, see WO 94/07529, and U.S. Pat. No. 4,962,091 the disclosures of which are incorporated by reference herein), can be administered by a variety of routes including parenteral, including by intravenous and intramuscular routes, as well as by direct injection into the diseased tissue. For example, the therapeutic agent may be directly injected into the tumor. The formulations may, where appropriate, be conveniently presented in discrete unit dosage forms and may be prepared by any of the methods well known to pharmacy. Such methods may include the step of bringing into association the therapeutic agent with liquid carriers, solid matrices, semi-solid carriers, finely divided solid carriers or combinations thereof, and then, if necessary, introducing or shaping the product into the desired delivery system.

When the therapeutic agents of the invention are prepared for administration, they are preferably combined with a pharmaceutically acceptable carrier, diluent or excipient to form a pharmaceutical formulation, or unit dosage form. The total active ingredients in such formulations include from 0.1 to 99.9% by weight of the formulation. A "pharmaceutically acceptable" is a carrier, diluent, excipient, and/or salt that is compatible with the other ingredients of the formulation, and not deleterious to the recipient thereof. The active ingredient for administration may be present as a powder or as granules; as a solution, a suspension or an emulsion.

Pharmaceutical formulations containing the therapeutic agents of the invention can be prepared by procedures known in the art using well known and readily available ingredients. The therapeutic agents of the invention can also be formulated as solutions appropriate for parenteral administration, for instance by intramuscular, subcutaneous or intravenous routes.

The pharmaceutical formulations of the therapeutic agents of the invention can also take the form of an aqueous or anhydrous solution or dispersion, or alternatively the form of an emulsion or suspension.

Thus, the therapeutic agent may be formulated for parenteral administration (e.g., by injection, for example, bolus injection or continuous infusion) and may be presented in unit dose form in ampules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

It will be appreciated that the unit content of active ingredient or ingredients contained in an individual aerosol dose of each dosage form need not in itself constitute an effective amount for treating the particular indication or disease since the necessary effective amount can be reached by administration of a plurality of dosage units. Moreover, the effective amount may be achieved using less than the dose in the dosage form, either individually, or in a series of administrations.

The pharmaceutical formulations of the present invention may include, as optional ingredients, pharmaceutically acceptable carriers, diluents, solubilizing or emulsifying agents, and salts of the type that are well-known in the art. Specific non-limiting examples of the carriers and/or diluents that are useful in the pharmaceutical formulations of the present invention include water and physiologically acceptable buffered saline solutions, such as phosphate buffered saline solutions pH 7.0-8.0.

The expression vectors, transduced cells, polynucleotides and polypeptides (active ingredients) of this invention can be formulated and administered to treat a variety of disease states by any means that produces contact of the active ingredient with the agent's site of action in the body of the organism. They can be administered by any conventional means available for use in conjunction with pharmaceuticals, either as individual therapeutic active ingredients or in a combination of therapeutic active ingredients. They can be administered alone, but are generally administered with a pharmaceutical carrier selected on the basis of the chosen route of administration and standard pharmaceutical practice.

In general, water, suitable oil, saline, aqueous dextrose (glucose), and related sugar solutions and glycols such as propylene glycol or polyethylene glycols are suitable carriers for parenteral solutions. Solutions for parenteral administration contain the active ingredient, suitable stabilizing agents and, if necessary, buffer substances. Antioxidizing agents such as sodium bisulfate, sodium sulfite or ascorbic acid, either alone or combined, are suitable stabilizing agents. Also used are citric acid and its salts and sodium Ethylenediaminetetraacetic acid (EDTA). In addition, parenteral solutions can contain preservatives such as benzalkonium chloride, methyl- or propyl-paraben and chlorobutanol. Suitable pharmaceutical carriers are described in Remington's Pharmaceutical Sciences, a standard reference text in this field.

The active ingredients of the invention may be formulated to be suspended in a pharmaceutically acceptable composition suitable for use in mammals and in particular, in humans. Such formulations include the use of adjuvants such as muramyl dipeptide derivatives (MDP) or analogs that are described in U.S. Pat. Nos. 4,082,735; 4,082,736; 4,101,536; 4,185,089; 4,235,771; and 4,406,890. Other adjuvants, which are useful, include alum (Pierce Chemical Co.), lipid A, trehalose dimycolate and dimethyldioctadecylammonium bromide (DDA), Freund's adjuvant, and IL-12. Other components may include a polyoxypropylene-polyoxyethylene block polymer (Pluronic®), a non-ionic surfactant, and a metabolizable oil such as squalene (U.S. Pat. No. 4,606,918).

Additionally, standard pharmaceutical methods can be employed to control the duration of action. These are well known in the art and include control release preparations and can include appropriate macromolecules, for example polymers, polyesters, polyamino acids, polyvinyl, pyrolidone, ethylenevinylacetate, methyl cellulose, carboxymethyl cellulose or protamine sulfate. The concentration of macromolecules as well as the methods of incorporation can be adjusted in order to control release. Additionally, the agent can be incorporated into particles of polymeric materials such as polyesters, polyamino acids, hydrogels, poly (lactic acid) or ethylenevinylacetate copolymers. In addition to being incorporated, these agents can also be used to trap the compound in microcapsules.

Accordingly, the pharmaceutical composition of the present invention may be delivered via various routes and to various sites in an mammal body to achieve a particular effect (see, e.g., Rosenfeld et al., 1991; Rosenfeld et al., 1991a; Jaffe et al., supra; Berkner, supra). One skilled in the art will recognize that although more than one route can be used for administration, a particular route can provide a more immediate and more effective reaction than another route. Local or systemic delivery can be accomplished by administration comprising application or instillation of the formulation into body cavities, inhalation or insufflation of an aerosol, or by parenteral introduction, comprising intramuscular, intravenous, peritoneal, subcutaneous, intradermal, as well as topical administration.

The active ingredients of the present invention can be provided in unit dosage form wherein each dosage unit, e.g., a teaspoonful, tablet, solution, or suppository, contains a predetermined amount of the composition, alone or in appropriate combination with other active agents. The term "unit dosage form" as used herein refers to physically discrete units suitable as unitary dosages for human and mammal subjects, each unit containing a predetermined quantity of the compositions of the present invention, alone or in combination with other active agents, calculated in an amount sufficient to produce the desired effect, in association with a pharmaceutically acceptable diluent, carrier, or vehicle, where appropriate. The specifications for the unit dosage forms of the present invention depend on the particular effect to be achieved and the particular pharmacodynamics associated with the pharmaceutical composition in the particular host.

These methods described herein are by no means all-inclusive, and further methods to suit the specific application will be apparent to the ordinary skilled artisan. Moreover, the effective amount of the compositions can be further approximated through analogy to compounds known to exert the desired effect.

Gene Therapy Administration

One skilled in the art recognizes that different methods of delivery may be utilized to administer a vector into a cell. Examples include: (1) methods utilizing physical means, such as electroporation (electricity), a gene gun (physical force) or applying large volumes of a liquid (pressure); and (2) methods wherein said vector is complexed to another entity, such as a liposome, aggregated protein or transporter molecule.

Furthermore, the actual dose and schedule can vary depending on whether the compositions are administered in combination with other pharmaceutical compositions, or depending on interindividual differences in pharmacokinetics, drug disposition, and metabolism. Similarly, amounts can vary in in vitro applications depending on the particular cell line utilized (e.g., based on the number of vector receptors present on the cell surface, or the ability of the particular vector employed for gene transfer to replicate in that cell line). Furthermore, the amount of vector to be added per cell will likely vary with the length and stability of the therapeutic gene inserted in the vector, as well as also the nature of the sequence, and is particularly a parameter which needs to be determined empirically, and can be altered due to factors not inherent to the methods of the present invention (for instance, the cost associated with synthesis). One skilled in the art can easily make any necessary adjustments in accordance with the exigencies of the particular situation.

Cells containing the therapeutic agent may also contain a suicide gene i.e., a gene which encodes a product that can be used to destroy the cell. In many gene therapy situations, it is desirable to be able to express a gene for therapeutic purposes in a host, cell but also to have the capacity to destroy the host cell at will. The therapeutic agent can be linked to a suicide gene, whose expression is not activated in the absence of an activator compound. When death of the cell in which both the agent and the suicide gene have been introduced is desired, the activator compound is administered to the cell thereby activating expression of the suicide gene and killing the cell. Examples of suicide gene/prodrug combinations which may be used are herpes simplex virus-thymidine kinase (HSV-tk) and ganciclovir, acyclovir; oxidoreductase and cycloheximide; cytosine deaminase and 5-fluorocytosine; thymidine kinase thymidilate kinase (Tdk::Tmk) and AZT; and deoxycytidine kinase and cytosine arabinoside.

These methods described herein are by no means all-inclusive, and further methods to suit the specific application will be apparent to the ordinary skilled artisan. Moreover, the effective amount of the compositions can be further approximated through analogy to compounds known to exert the desired effect.

EXAMPLES

The invention is now described with reference to the following Examples. These Examples are provided for the purpose of illustration only, and the invention is not limited to these Examples, but rather encompasses all variations which are evident as a result of the teachings provided herein.

The following experiments were designed to evaluate the capacity of the immune system to recognize aberrantly expressed ES genes in an adult. The results presented herein demonstrate that most healthy humans harbor OCT4 specific T cells that are readily detectable in freshly isolated blood mononuclear cells and demonstrate the alteration of these responses in vivo in patients undergoing curative therapy for germ cell tumors.

The materials and methods employed in the experiments disclosed herein are now described.

Healthy Donors and Patients with Germ Cell Tumors

Peripheral blood was collected from healthy donors as well as patients with germ cell tumors (GCTs), after obtaining informed consent approved by the Institutional Review Boards at Yale University, The Rockefeller University, or the Memorial Sloan Kettering Cancer Center (New York, N.Y.). Buffy coats derived from healthy blood donors were purchased from the New York Blood Center (New York, N.Y.).

Synthesis of OCT4 Peptide Library

Peptides were synthesized in the Proteomics Resource Center at the Rockefeller University, New York, N.Y., as described in Spisek et al., 2007 J Exp Med 204(4): 831-40. Overlapping sequences from the OCT4 protein were determined and optimized for synthesis by utilizing an epitope library fragment generation program PeptGen™ developed by Los Alamos National Laboratories, Los Alamos, N. Mex. as part of the HIV Immunology Database at http://www.hiv-.lanl.gov. All peptides were created in microtiter plate (96 well) format using an Intavis MultiPep™ parallel peptide synthesizer/spotter (Intavis, Koln, Germany) on pre-coupled Wang (p-Alkoxy-benzyl alcohol) resins (Bachem, Torrance, Calif.) loaded at 10 µMol per well, using Fmoc protected amino acids (Anaspec, San Jose, Calif.). Deprotection of the amine was accomplished with 20% piperidine (Aldrich) in NMP (Nmethylpyrrolidinone). Repetitive coupling reactions were conducted using 0.6 M HATU/HOBT and 0.4 M NMM using NMP (EMD) as the primary solvent. Simultaneous resin cleavage and side-chain deprotection were achieved by treatment with 0.8 ml/well concentrated, sequencing grade, trifluoroacetic acid (Fisher) with triisopropylsilane (Fluka), water, and 3,6 dioxa-1,8-octane-dithiol (DODT, Aldrich) in a ratio of 95:2:2:1 over a 4 hour time frame. Following vacuum filtration to a collection plate, a standard ether precipitation was performed on all individual peptides in 10 ml cold tert-butyl methyl ether (TBME, Aldrich). After pellet formation by centrifugation, excess ether was removed by vacuum aspiration. Peptides were then treated with 0.5 ml 8 M acetic acid and washed with 10 ml of cold TBME again. The precipitates were again allowed to form and spun. The excess ether was then removed and the pellets allowed to dry overnight. Peptide pellets were redissolved in 20% acetonitrile and HPLC grade water and lyophilized. All crude products were subsequently analyzed by reversed-phase HPLC (Waters Chromatography, Milford, Mass.) using a Merck Chromolith™ Performance C18 column. Individual peptide integrity was verified by matrix-assisted laser desorption ionization (MALDI) mass spectrometry using a PerSeptive/Applied Biosystems Voyager™ (PE/ABI, Foster City, Calif.) delayed extraction spectrometer system. The library consisted of 95 peptides (15-mer overlapping by 11 amino acids), and was divided into four submixes of pooled peptides as follows: Mix 1, peptides 1 to 25; Mix 2, peptides 26 to 50; Mix 3, peptides 51 to 75; and Mix 4, peptides 76 to 95. The sequences of individual peptides in this library are noted in Table 1.

TABLE 1

Sequences of peptides in OCT4 library

| Peptide No. | Peptide sequence | SEQ ID NO |
|---|---|---|
| 1. | MAGHLASDFAFSPPP | SEQ ID NO: 1 |
| 2. | LASDFAFSPPPGGGG | SEQ ID NO: 2 |
| 3. | FAFSPPPGGGGDGP | SEQ ID NO: 3 |
| 4. | SPPPGGGGDGPGGP | SEQ ID NO: 4 |
| 5. | PGGGGDGPGGPEPGW | SEQ ID NO: 5 |
| 6. | GDGPGGPEPGWVDPR | SEQ ID NO: 6 |
| 7. | GGPEPGWVDPRTWLS | SEQ ID NO: 7 |
| 8. | PGWVDPRTWLSFQGP | SEQ ID NO: 8 |
| 9. | DPRTWLSFQGPPGGP | SEQ ID NO: 9 |
| 10. | WLSFQGPPGGPGIGP | SEQ ID NO: 10 |
| 11. | FQGPPGGPGIGPGV | SEQ ID NO: 11 |
| 12. | PPGGPGIGPGVGPGS | SEQ ID NO: 12 |
| 13. | PGIGPGVGPGSEVW | SEQ ID NO: 13 |
| 14. | GPGVGPGSEVWGIPP | SEQ ID NO: 14 |
| 15. | GPGSEVWGIPPCPPP | SEQ ID NO: 15 |
| 16. | EVWGIPPCPPPYEFC | SEQ ID NO: 16 |

TABLE 1-continued

Sequences of peptides in OCT4 library

| Peptide No. | Peptide sequence | SEQ ID NO |
|---|---|---|
| 17. | IPPCPPPYEFCGGMA | SEQ ID NO: 17 |
| 18. | PPPYEFCGGMAYCGP | SEQ ID NO: 18 |
| 19. | EFCGGMAYCGPQVGV | SEQ ID NO: 19 |
| 20. | GMAYCGPQVGVGLVP | SEQ ID NO: 20 |
| 21. | CGPQVGVGLVPQGGL | SEQ ID NO: 21 |
| 22. | VGVGLVPQGGLETS | SEQ ID NO: 22 |
| 23. | GLVPQGGLETSQP | SEQ ID NO: 23 |
| 24. | VPQGGLETSQPEGEA | SEQ ID NO: 24 |
| 25. | GLETSQPEGEAGVGV | SEQ ID NO: 25 |
| 26. | SQPEGEAGVGVESNS | SEQ ID NO: 26 |
| 27. | GEAGVGVESNSDGAS | SEQ ID NO: 27 |
| 28. | VGVESNSDGASPEPC | SEQ ID NO: 28 |
| 29. | SNSDGASPEPCTVTP | SEQ ID NO: 29 |
| 30. | GASPEPCTVTPGAVK | SEQ ID NO: 30 |
| 31. | EPCTVTPGAVKLEK | SEQ ID NO: 31 |
| 32. | TVTPGAVKLEKEKL | SEQ ID NO: 32 |
| 33. | PGAVKLEKEKLEQNP | SEQ ID NO: 33 |
| 34. | KLEKEKLEQNPEES | SEQ ID NO: 34 |
| 35. | KEKLEQNPEESQDIK | SEQ ID NO: 35 |
| 36. | EQNPEESQDIKALQK | SEQ ID NO: 36 |
| 37. | EESQDIKALQKEL | SEQ ID NO: 37 |
| 38. | SQDIKALQKELEQFA | SEQ ID NO: 38 |
| 39. | KALQKELEQFAKLLK | SEQ ID NO: 39 |
| 40. | KELEQFAKLLKQKRI | SEQ ID NO: 40 |
| 41. | EQFAKLLKQKRITL | SEQ ID NO: 41 |
| 42. | AKLLKQKRITLGYT | SEQ ID NO: 42 |
| 43. | LKQKRITLGYTQADV | SEQ ID NO: 43 |
| 44. | RITLGYTQADVGLTL | SEQ ID NO: 44 |
| 45. | GYTQADVGLTLGVLF | SEQ ID NO: 45 |
| 46. | ADVGLTLGVLFGKVF | SEQ ID NO: 46 |
| 47. | LTLGVLFGKVFSQTT | SEQ ID NO: 47 |
| 48. | VLFGKVFSQTTICRF | SEQ ID NO: 48 |
| 49. | KVFSQTTICRFEAL | SEQ ID NO: 49 |
| 50. | SQTTICRFEALQLSF | SEQ ID NO: 50 |
| 51. | ICRFEALQLSFKNMC | SEQ ID NO: 51 |
| 52. | EALQLSFKNMCKLRP | SEQ ID NO: 52 |
| 53. | LSFKNMCKLRPLLQK | SEQ ID NO: 53 |
| 54. | NMCKLRPLLQKWV | SEQ ID NO: 54 |
| 55. | CKLRPLLQKWVEEA | SEQ ID NO: 55 |
| 56. | RPLLQKWVEEADNNENL | SEQ ID NO: 56 |
| 57. | WVEEADNNENLQEIC | SEQ ID NO: 57 |
| 58. | ADNNENLQEICKAET | SEQ ID NO: 58 |
| 59. | ENLQEICKAETLVQA | SEQ ID NO: 59 |
| 60. | EICKAETLVQARKRK | SEQ ID NO: 60 |
| 61. | AETLVQARKRKRTSI | SEQ ID NO: 61 |
| 62. | VQARKRKRTSIENRV | SEQ ID NO: 62 |
| 63. | KRKRTSIENRVRGNL | SEQ ID NO: 63 |
| 64. | TSIENRVRGNLENLF | SEQ ID NO: 64 |
| 65. | NRVRGNLENLFLQCP | SEQ ID NO: 65 |
| 66. | GNLENLFLQCPKPTL | SEQ ID NO: 66 |
| 67. | NLFLQCPKPTLQQIS | SEQ ID NO: 67 |
| 68. | LQCPKPTLQQISHIA | SEQ ID NO: 68 |
| 69. | KPTLQQISHIAQQL | SEQ ID NO: 69 |
| 70. | LQQISHIAQQLGLEK | SEQ ID NO: 70 |
| 71. | SHIAQQLGLEKDVVR | SEQ ID NO: 71 |
| 72. | AQQLGLEKDVVRVWF | SEQ ID NO: 72 |
| 73. | GLEKDVVRVWFCNRR | SEQ ID NO: 73 |
| 74. | DVVRVWFCNRRQKGK | SEQ ID NO: 74 |
| 75. | VWFCNRRQKGKRSSS | SEQ ID NO: 75 |
| 76. | NRRQKGKRSSSDYA | SEQ ID NO: 76 |
| 77. | RQKGKRSSSDYAQR | SEQ ID NO: 77 |
| 78. | GKRSSSDYAQREDF | SEQ ID NO: 78 |
| 79. | SSSDYAQREDFEAA | SEQ ID NO: 79 |
| 80. | DYAQREDFEAAGSPF | SEQ ID NO: 80 |
| 81. | REDFEAAGSPFSGGP | SEQ ID NO: 81 |
| 82. | EAAGSPFSGGPVSFP | SEQ ID NO: 82 |
| 83. | SPFSGGPVSFPLAP | SEQ ID NO: 83 |
| 84. | SGGPVSFPLAPGPHF | SEQ ID NO: 84 |
| 85. | VSFPLAPGPHFGTP | SEQ ID NO: 85 |
| 86. | PLAPGPHFGTPGYGS | SEQ ID NO: 86 |
| 87. | GPHFGTPGYGSPHFT | SEQ ID NO: 87 |
| 88. | GTPGYGSPHFTALYS | SEQ ID NO: 88 |
| 89. | YGSPHFTALYSSVPF | SEQ ID NO: 89 |
| 90. | HFTALYSSVPFP | SEQ ID NO: 90 |
| 91. | FTALYSSVPFPEGEA | SEQ ID NO: 91 |
| 92. | YSSVPFPEGEAFPPV | SEQ ID NO: 92 |

TABLE 1-continued

Sequences of peptides in OCT4 library

| Peptide No. | Peptide sequence | SEQ ID NO |
|---|---|---|
| 93. | PFPEGEAFPPVSVTT | SEQ ID NO: 93 |
| 94. | GEAFPPVSVTTLGSP | SEQ ID NO: 94 |
| 95. | PPVSVTTLGSPMHSN | SEQ ID NO: 95 |

Mix 1, peptides 1 to 25; Mix 2, peptides 26 to 50; Mix 3, peptides 51 to 75; and Mix 4, peptides 76 to 95.

Detection for OCT4 Reactive T Cells in Fresh PBMCs

Peripheral Blood Mononuclear cells (PBMCs) were separated by density gradient centrifugation using Ficoll-Hypaque (GE HealthCare). 2×10$^5$ PBMCs in 200 µl of media were cultured in the presence of 3 µg/ml of peptide pools derived from OCT4 peptide library. A mixture of MHC class I restricted peptides derived from influenza virus, EBV and CMV (CEF mix), or phytohemagglutinin (PHA) were used as positive controls (Spisek et al., 2007 J Exp Med 204(4): 831-40). The composition of the OCT4 peptide library pools is noted in Table 1. After 48 hrs, supernatants were collected and assayed for the production of interferon-γ inducible protein 10 (IP10) by Luminex, using the manufacturer's directions (Luminex Corp and Upstate), and analyzed by Beadview software (Upstate). In some experiments, CD3+ T cells were depleted by negative selection, or stimulation by specific antigens was carried out in the presence of IFNγ-blocking mAbs (Biolegend) to confirm the specificity of IP10 production. In the assay validation experiments, the variation between replicates, including the nonreactive submixes (intraassay), as well as reanalysis of the same sample (interassay), was analyzed. The coefficient of variation (% CV) in these experiments was mean (range) 8.5% (4-23%) for intraassay and 6% (1.5-30%) for interassay measurements. Based on these considerations, ≥2-fold increase in IP10 production, with a minimal absolute measurement of 100 pg/mL, was predetermined to be positive for the presence of antigen-specific T cells, as previously described (Spisek et al., 2007 J Exp Med 204(4): 831-40). In several donors, the reactivity to a submix was further confirmed by individually testing each individual peptide from the reactive submix, to identify the specific peptide responsible for the reactivity.

CFSE Proliferation Assay

PBMCs obtained as described above were labeled with CFSE cell tracker dye (carboxyfluorescein diacetate succinimidyl ester; 0.5 µM; Molecular probes, Eugene, Oreg.) to monitor proliferation. CFSE labeled PBMCs were cultured with 1 µg/ml of anti-CD28 and anti-CD49d (BD biosciences; San Jose, Calif.) alone or with Oct4 peptide mixes (3 µg/ml), CEF mix (3 µg/ml) or PHA (2 µg/ml). After 7 days of culture, PBMCs were stained with anti-CD3, CD4 and T cell proliferation was analyzed using the FACSCalibur (Becton Dickinson). The data was analyzed using the FlowJo software.

Dendritic Cell Generation and Expansion of OCT4 Specific T Cells

DCs were generated from monocytes isolated by CD14 magnetic beads (Miltenyi Biotech) and cultured for 5 days in the presence of GM-CSF (Immunex) and IL-4 (R&D Systems), as described in Spisek et al., 2007 J Exp Med 204: 831-840. Day-5 DC were matured overnight with inflammatory cytokines [10 ng/mL IL-1β, 1,000 U/mL IL-6, 10 ng/mL TNF-α, (all from R&D Systems), and prostaglandin E2 (1 µg/mL, Sigma-Aldrich)] and pulsed for 2 h with OCT4-derived peptide; 2 µg/mL CD14-responder T cell-enriched fraction was added to U-bottom 96-well plates at 2×10$^5$ cells per well in 200 µL of medium and stimulated with mature peptide pulsed DC at DC: responder ratio of 1:30. IL2 (20 U/mL) was added to the DC:T-cell cocultures on days 4, 7, and 14. IL7 and IL15 (both 5 ng/mL) were added on day 14. After two restimulations with peptide-loaded DCs, the T cells were analyzed for the presence of peptide-reactive T cells using intracellular cytokine assay. For some experiments, immature DCs were fed with irradiated embryonal carcinoma tumor cells (N-tera), before maturation and use as antigen-presenting cells to stimulate autologous T cells (Dhodapkar et al., 2002 J Exp Med 195: 125-133).

Flow Cytometry for the Detection of Intracellular Cytokines

Antigen specific cells were analyzed by flow cytometry-based assay for the detection of intracellular cytokines as described in Chang et al., 2005 J Exp Med 201(9): 1503-17. Briefly, T cells were cultured with anti-CD28 anti-CD49d (both at 5 µg/ml, BD Biosciences), alone or with OCT4 peptides (3 µg/ml) in the presence of Brefeldin A. After 5 hrs in culture, T cells were fixed and permeabilized in 100 µl Cytofix/Cytoperm solution using manufacturer's instructions and stained for intracellular IFN-γ and surface markers (CD3, CD8). The presence of peptide-specific IFNγ-producing T cells was analyzed by flow cytometry. In some experiments, mature DCs alone or loaded with OCT4Mix 3 were used to assess the generation of OCT4-specific T cells.

Statistical Analysis

The reactivity against OCT4 between two groups was compared using Mann Whitney test, and significance set at $p<0.05$.

The results of the experiments presented in this Example are now described.

Example 1: OCT4-Specific Immune Response

OCT4 is a transcription factor critical for the pluripotency of human embryonal stem (ES) and induced pluipotency stem (IPS) cells. OCT4 is commonly expressed in germ-cell tumors as well as putative cancer stem cells in several tumors, and is a key determinant of oncogenic fate in germ-cell tumors. The capacity of the human immune system to recognize this critical stem-cell gene is not known, but has implications for preventing tumors with ES/IPS-based therapies and targeting stem-cell pathways in cancer. The results presented herein demonstrate that OCT4-specific T cells can be readily detected in freshly isolated T cells from most (>80%) healthy donors. The reactivity to OCT4-derived peptides resides primarily in the CD45RO+ memory T-cell compartment and consists predominantly of CD4+ T cells. T cells reactive against OCT4-derived peptides can be readily expanded in culture using peptide-loaded dendritic cells. In contrast to healthy donors, immunity to OCT4 was detected in only 35% of patients with newly diagnosed germ-cell tumors. However, chemotherapy of germ-cell tumors led to the induction of anti-OCT4 immunity in vivo in patients lacking such responses at baseline. These data demonstrate the surprising lack of immune tolerance to this critical pluripotency antigen in humans. Without wishing to be bound by any particular theory, it is believed that harnessing natural immunity to this antigen allows immune-based targeting of pluripotency-related pathways for prevention of cancers, including those in the setting of ES/IPSbased therapies.

Figure 2:
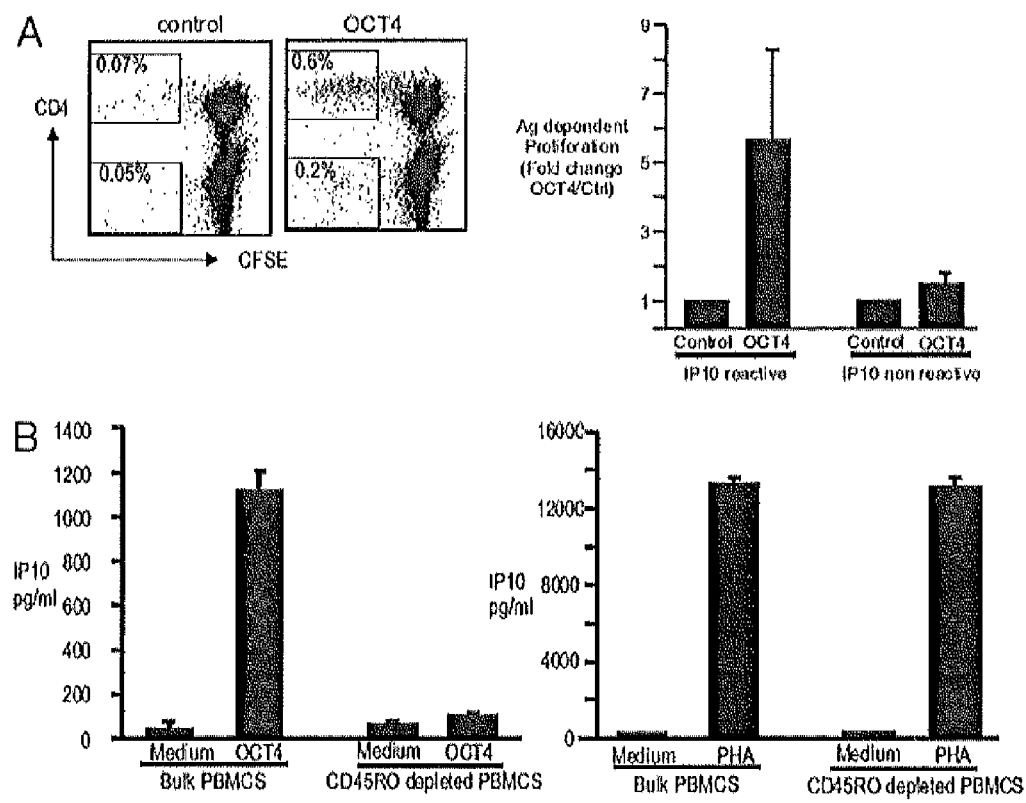
FIG. 2, comprising

To analyze the capacity of human T cells to recognize OCT4, mononuclear cells from healthy blood donors (n=30) were cultured with an overlapping peptide library spanning the entire OCT4 protein (see Table 1 for the sequences of peptides in this library), and culture supernatants assayed for the presence of IFN-γ inducible protein-10 (IP10). Positive reactivity in this assay was defined as ≥2-fold increase in IFN-γ IP10 production in the reactive mix versus control, with a minimal absolute measurement of 100 pg/mL predetermined to be positive for the presence of antigen-specific T cells. Using this cutoff, reactivity against peptide pools derived from this library was detectable in 25 of 30 (83%) donors tested (FIGS. 1A and 1B). Peptide reactive IP10 production was abrogated upon depletion of CD3+ T cells before stimulation (FIG. 1C), as well as blockade of IFN-γ (FIG. 1D), demonstrating that the reactivity in this assay was dependent on peptide reactive production of IFNγ by T cells. Analysis of peptide reactive proliferation indicated that the proliferating T cells were predominantly CD4+ T cells, and antigen-dependent proliferation correlated with reactivity in the IP10 assay (FIG. 2A). The rapidity of cytokine production in response to antigen stimulation suggested that the observed immune response was a memory T-cell response. To further evaluate this finding, bulk PBMCs were depleted of CD45RO+ T cells before stimulation with OCT4 peptide library [or phytoagglutinin (PHA) as a control]. Depletion of CD45RO+ T cells led to abrogation of OCT4 reactivity, suggesting that the OCT4-specific response as measured in this assay resided predominantly in the CD45RO+ subpopulation (FIG. 2B). Together, these data indicate the presence of OCT4-specific memory T-cell response, which can be readily detected in freshly isolated PBMCs from healthy donors.

Figure 3:
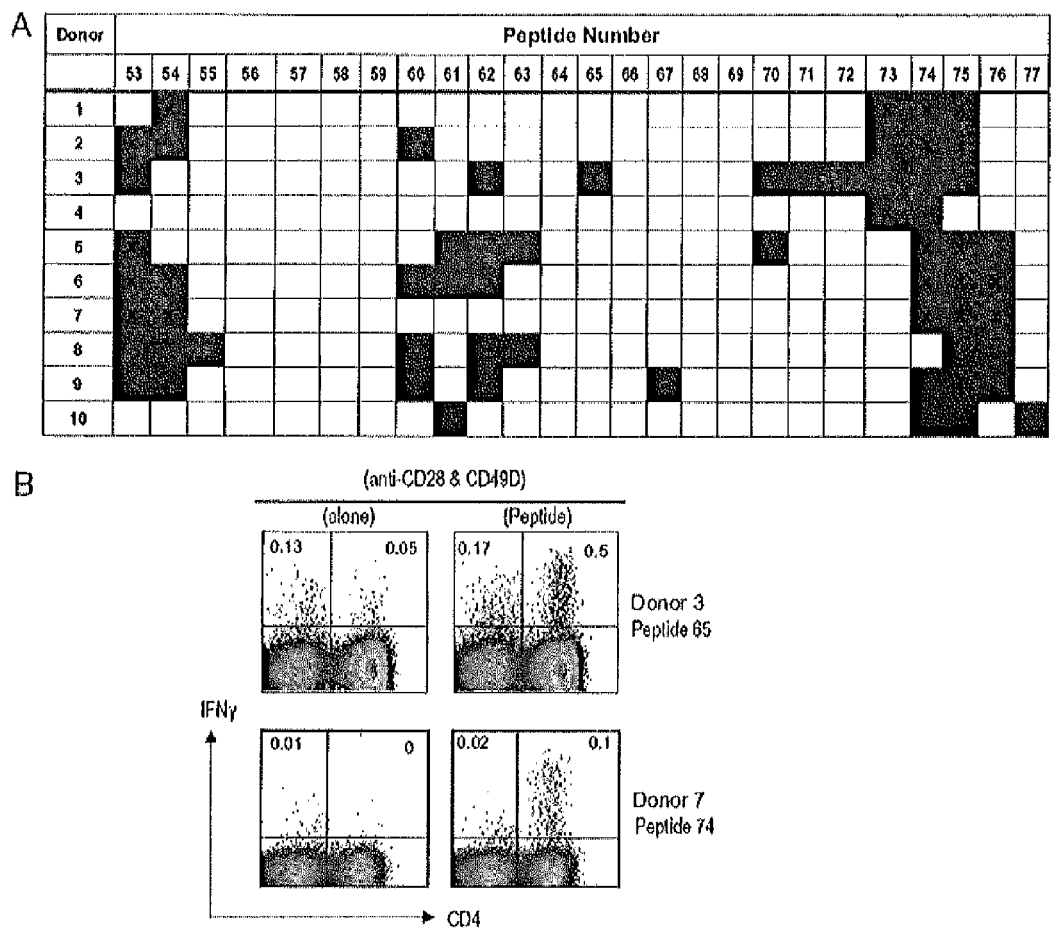
FIG. 3, comprising

To analyze the fine specificity of the anti-OCT4 response and confirm reactivity to the peptide mix, PBMCs were cultured against individual peptides from the reactive peptide mix in 10 donors. Although individual donors had reactivity to different peptides within the pool, some hot-spot areas of promiscuous reactivity were also identified (FIG. 3A). Analysis of areas of hot spots of reactivity by BLAST (National Center for Biotechnology Information) demonstrated that these sequences represented highly conserved regions within OCT4 protein, without homology to known pathogen-derived sequences. To further analyze the capacity of functional OCT4-specific T cells to expand in culture, T cells were stimulated with peptide-pulsed autologous dendritic cells (DCs). The presence of peptide-specific IFNγ-secreting CD4+ T cells was then analyzed by intracellular cytokine flow cytometry following peptide-specific restimulation (FIG. 3B). Together, these data demonstrate that T cells responding to peptide epitopes derived from OCT4 can be readily detected and expanded in culture using stimulation with peptide-loaded autologous DCs. Together, these data demonstrate the lack of immune tolerance to this critical ES antigen in humans, and show that these T cells can be readily harnessed for potential therapeutic utility after ex vivo stimulation.

Figure 4:
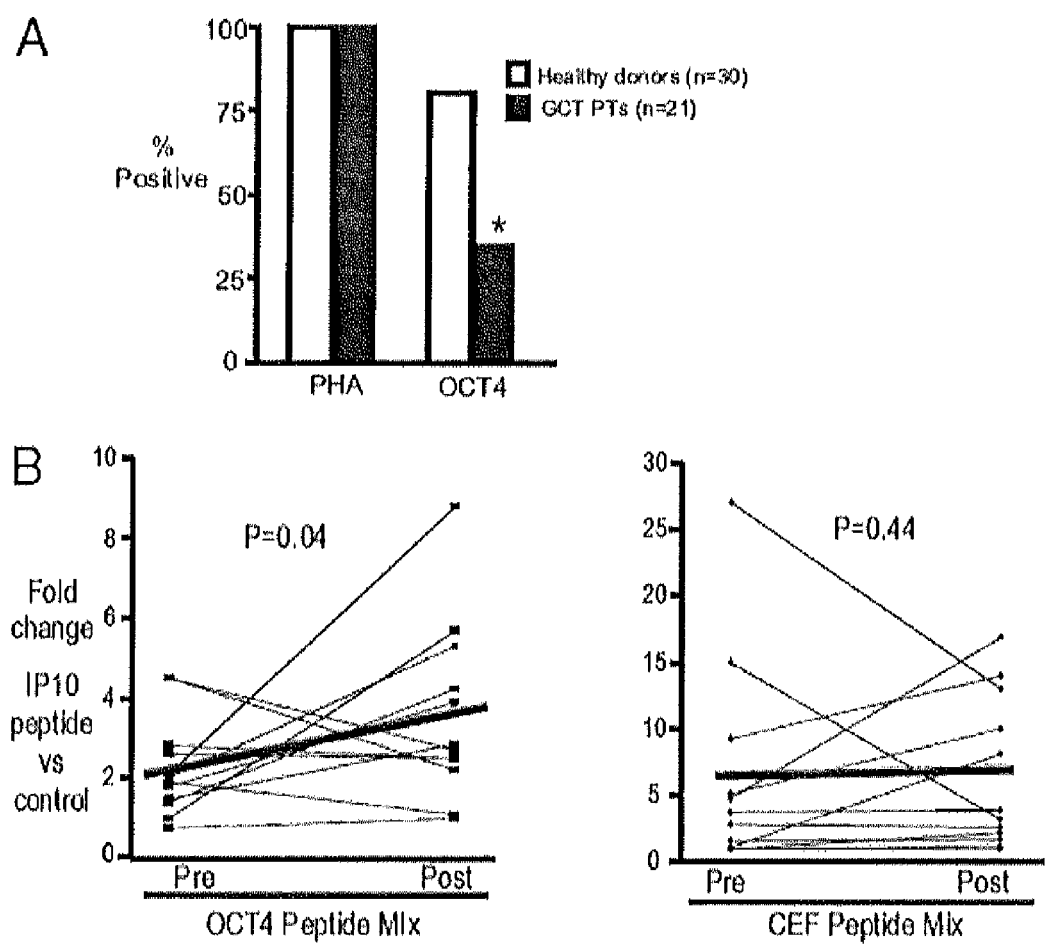
FIG. 4, comprising

OCT4 has emerged as an important biomarker and critical determinant of oncogenic fate in GCTs (de Jong et al. 2006 Crit Rev Oncog 12: 171-203; Clark, 2007 Stem Cell Rev 3: 49-59). Therefore, experiments were designed to prospectively analyzed the presence of OCT4-specific T cells in patients with newly diagnosed GCT, at baseline and after the completion of therapy. Of 21 patients analyzed, 20 had pathologic evidence for predominant seminoma or embryonal carcinoma, subtypes typically associated with highest OCT4 expression (Table 2) (de Jong et al. 2006 Crit Rev Oncog 12: 171-203). Reactivity to viral antigens (CMV, EBV, and influenza; CEF) and PHA was monitored as a control. In contrast to the finding with healthy donors, only 8 of 21 patients with GCT (38%) had measurable OCT4-specific T cell immunity at baseline (P<0.05) (FIG. 4A). An intriguing aspect of GCTs is the high curability of these tumors, even in the setting of advanced cancers (Masters et al., 2003 Nat Rev Cancer 3: 517-525). Recent studies have suggested that the ability of some chemotherapies to induce immunogenic death of tumor cells may contribute to their antitumor effects in vivo (Zitvogel et al., 2008 Nat Rev Immunol 8: 59-73). However, whether specific immunity to tumor-associated antigens is induced after curative therapy for GCT is not known. In contrast to analysis of baseline samples, the presence of OCT4-specific T cells was detected at the completion of chemotherapy in 10 of 12 patients (83%) tested, including 5 patients who lacked such responses at baseline (FIG. 4B). The induction of antigen-specific T cells after therapy was specific for OCT4, as there were no significant changes in virus-specific T-cell responses (FIG. 4B).

Figure 5:
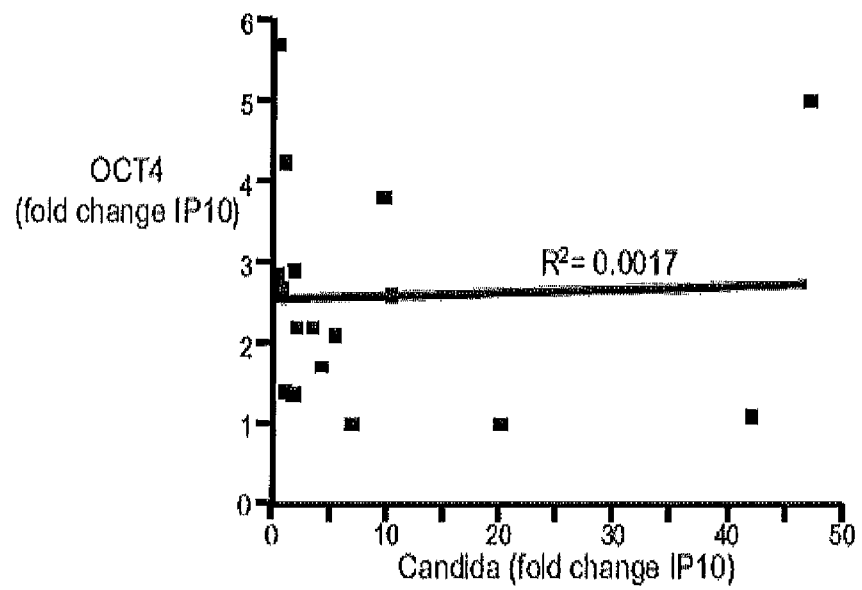
FIG. 5 is an image depicting lack of correlation between OCT4 reactivity and CD4+ T-cell immunity to candida. Data for OCT4 reactivity (fold-change in inducible protein-10 production) as in FIG. 4 is plotted against the data for CD4+ T-cell reactivity to candida.
Figure 6:
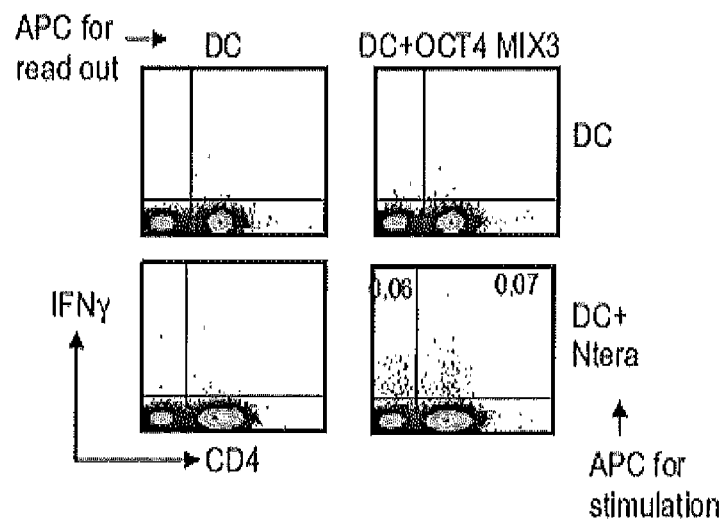
FIG. 6 is an image depicting induction of OCT4-specific T cells by tumor-loaded dendridic cells (DCs). Monocyte-derived DCs alone (DC) or fed with irradiated embryonal carcinoma (N-tera) cells (DC+Ntera), and used to stimulate autologous T cells. Induction of OCT4-specific T cells was monitored using intracellular cytokine flow cytometry in response to autologous DCs alone or loaded with OCT4 peptide Mix 3.

There was also no correlation between reactivity to OCT4 and candida, as an additional control for human antigen-specific CD4+ T-cell responses (r2=0.002) (FIG. 5). Without wishing to be bound by any particular theory, it is believed that the induction of OCT4-specific T cells involves the uptake of dying tumor cells by DCs. Stimulation of autologous T cells with DCs loaded with dying embryonal carcinoma cells led to the induction of OCT4-specific immune responses in culture (FIG. 6). Therefore, DCs can process and present OCT4 from dying GCT cells. Together, these data suggest that chemotherapy-induced cell death may lead to the induction of tumor immunity in vivo.

TABLE 2

Clinical characteristics of patients with germ cell tumors:

| Pt ID | Age (Yrs) | Primary Site | Histologic Diagnosis | Treatment |
| --- | --- | --- | --- | --- |
| GCT1 | 53 | Testis | Seminoma | chemotherapy |
| GCT2 | 45 | Testis | Mixed NSGCT: EC (95%) and seminoma | chemotherapy |
| GCT3 | 36 | Testis | Seminoma | chemotherapy |
| GCT4 | 28 | Testis | Mixed NSGCT: T (both MT and IT, dominant), EC (20%), and YST | chemotherapy |
| GCT5 | 35 | Testis | NSGCT: EC (100%) | chemotherapy |
| GCT6 | 24 | Testis | NSGCT: T (100%) | chemotherapy |
| GCT7 | 16 | Testis | NSGCT: EC (100%) | chemotherapy |
| GCT8 | 28 | Testis | Mixed NSGCT: EC (60%), seminoma, YST, and choriocarcinoma | chemotherapy |

TABLE 2-continued

Clinical characteristics of patients with germ cell tumors:

| Pt ID | Age (Yrs) | Primary Site | Histologic Diagnosis | Treatment |
|---|---|---|---|---|
| GCT9 | 58 | Testis | Seminoma | XRT |
| GCT10 | 43 | Testis | Seminoma | chemotherapy |
| GCT11 | 26 | Mediastinum | Seminoma | chemotherapy |
| GCT12 | 34 | Testis | Mixed NSGCT: EC (>98%) and seminoma | chemotherapy |
| GCT13 | 31 | Testis | Mixed NSGCT: EC, YST, and MT | chemotherapy |
| GCT14 | 29 | Testis | Mixed NSGCT: Seminoma (95%) and EC | chemotherapy |
| GCT15 | 39 | Mediastinum | Seminoma | chemotherapy |
| GCT16 | 16 | Testis | Mixed NSGCT: EC (80%), YST, and MT | chemotherapy |
| GCT17 | 40 | Testis | Seminoma | chemotherapy |
| GCT18 | 31 | Testis | NSGCT: EC (100%) | chemotherapy |
| GCT19 | 29 | Testis | Mixed NSGCT: EC (85%), YS, IT, seminoma, and syncytiotrophoblasts | chemotherapy |
| GCT20 | 30 | Mediastinum | Seminoma | chemotherapy |
| GCT21 | 28 | Testis | Mixed NSGCT: MT (>95%) and seminoma | chemotherapy |

(Abbreviations:
NSGCT: non-seminomatous germ cell tumor;
EC: embryonal carcinoma;
YST: Yolk sac tumor;
MT: mature teratoma;
IT: immature teratoma;
T: teratoma (not specified mature or immature);
XRT: radiation therapy; and
Yrs: years.
All patients were analyzed at baseline, and when possible, at completion of chemotherapy.
Numbers in parentheses represent the percentage of subhistologies within a mixed NSGCT as noted in the pathology report.
All patients responded to therapy.
Chemotherapy was based on cisplatin and etoposide combination.

Example 2: Natural Immunity to Pluripotency Antigen OCT4 in Humans

The results presented herein demonstrate that most healthy humans have naturally occurring memory T-cell responses to specific epitopes derived from OCT4, indicating that most individuals lack immune tolerance to this critical pluripotency antigen. Several studies have examined the presence of self-antigen reactive T cells in healthy individuals and patients with cancer or autoimmunity. Detection of T cells specific for MelanA/MART1 (CD8+, naive), carcinoembryonic antigen (CD4, naive), wildtype p53 (CD8/CD4, naive), cyclin B1 (CD4/CD8, naive/memory), glutamic acid decarboxylase, and insulin (CD4/CD8, naive) was feasible in T cells from healthy individuals (Pittet et al., 1999 J Exp Med 190: 705-715; Cicinnati et al. 2006 Int J Cancer 119: 2851-2860; Pickford et al., 2007 Clin Cancer Res 13: 4528-4537; Vella t al., 2009 Proc Natl Acad Sci USA 106: 14010-14015; Monti et al. 2007 J Immunol 179: 5785-5792). However, none of these nor similar studies evaluated the immunogenicity of ES-restricted antigens in humans or mice, which may provide a potential mechanism for immune-mediated surveillance against unrestrained growth of pluripotent cells, as well as GCT. The presence of rare OCT4-expressing cells with pluripotent potential in adult tissues has recently been suggested to play a role in tissue regeneration in mice (de Jong, 2006 Crit Rev Oncog 12: 171-203; Shin et al., 2009 Leukemia 23: 2042-2051; Kordes et al., 2009 Biol Chem 390: 1003-1012). It has been shown that T-cell responses against another ES antigen, SOX2, are commonly detected in patients with preneoplastic gammopathy and correlate with reduced risk of progression to overt myeloma (Spisek et al., 2007 J Exp Med 204: 831-840). However, in contrast to OCT4, anti-80×2 responses were not detected in healthy donors using similar assays (Spisek et al., 2007 J Exp Med 204: 831-840). The reason underlying the differences in immune reactivity between these two core ES factors in healthy individuals is not known, but may relate to differences in their immunogenicity, or patterns of aberrant expression (de Jong, 2006 Crit Rev Oncog 12: 171-203; Shin et al., 2009 Leukemia 23: 2042-2051; Kordes et al., 2009 Biol Chem 390: 1003-1012).

The results presented herein show that anti-OCT4 T cells are specifically induced in vivo in response to therapy of GCTs demonstrates that these T cells are functional in vivo and can respond to stimulation. Most of the OCT4-specific T cells consist of CD4+ T cells. As most testicular tumors are typically MHC II-negative (Nouri et al., 1993 Eur J Cancer 29A: 1895-1899), the induction of OCT4 T cells may involve the uptake of dying tumor cells and presentation of tumor-derived antigens by DCs. Tumor-specific CD4+ Th1 cells can mediate antitumor effects against MHC II negative cells by multiple mechanisms, including the activation of macrophage-mediated innate resistance and antiangiogenesis (Corthay et al., 2005 Immunity 22:371-383; Mumberg et al., 1999 Proc Natl Acad Sci USA 96: 8633-8638; Pardoll et al., 1998 Curr Opin Immunol 10: 588-594.). These data also provide evidence that curative therapy of GCTs can lead to the induction of tumor antigen-specific T-cell responses in vivo.

The results presented herein also have several therapeutic implications. Cells derived from IPS cells are likely to reach the clinic in the near future, but carry a real risk of tumor formation, particularly if the ES genes were to be reactivated in vivo (Knoepfler, 2009 Stem Cells 27: 1050-1056; Miura et al., 2009 Nat Biotechnol 27: 743-745). Boosting immunity to OCT4 may therefore be important to minimize the tumorigenicity of these cells in the clinic. A growing body of data points to the importance of shared pathways of "stemness" in the biology of human cancer and ES cells (Wang et al., 2008 Cell Stem Cell 2: 297-299; Reya et al., 2001 Nature 414: 105-111). OCT4 is essential for pluripotency of ES and IPS cells, OCT4 has been shown to act as a dose-dependent oncogenic fate determinant in mice and is believed to play a critical role in the pathogenesis of GCT (Gidekel et al., 2003 Cancer Cell 4: 361-370). However, interactions between transcriptional networks regulating pluripotency/stemness may be cell type/context-dependent, particularly in the setting of transformed cells. For example, pluripotency in some variant ES lines was found to be independent of OCT4 (Ji et al., 2009 PLoS One 4: e8065). Therefore, further study is needed to elucidate the functional significance of OCT4 expression in putative cancer stem cells in different cancers. An important consideration when targeting putative cancer stem-cell genes is the potential impact on normal stem cells. It is therefore of interest that OCT4 is dispensable for the function of adult stem cells in mice, making it an attractive target on cancer stem cells (Lengner et al., 2007 Cell Stem Cell 1: 403-415). There is a long history of targeting embryonal tissues toward vaccines against cancer, as reviewed recently (Brewer et al., 2009 Exp Mol Pathol 86: 192-197). Notably in these studies, the protective effect was most evident only with early but not late embryonic tissues and lacked precise definition of antigenic targets (Brewer et al., 2009 Exp Mol Pathol 86: 192-197). Interestingly, a recent study demonstrated that vaccination of mice with ES/IPS cells mediated protection in a colon-cancer model (Li et al., 2009 Stem Cells 27: 3103-3111). The immunogenic epitopes of OCT4 as identified here may therefore serve as the basis of a vaccine for prevention or therapy of several cancers, or adoptive T cell-based therapies, including in the setting of allogeneic stem cell transplantation. Immunity to stemness genes may be critical for harnessing the immune system against cancer.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A composition comprising a plurality of OCT4 peptides, each said OCT4 peptide consisting of a peptide selected from the group consisting of SEQ ID NO: 53 and SEQ ID NO: 74, and further comprising an adjuvant, and one or more pharmaceutically acceptable excipients.

2. The composition of claim 1, wherein the plurality of OCT4 peptides comprises a peptide consisting of SEQ ID NO:53 and a peptide consisting of SEQ ID NO:74.

3. A composition comprising a plurality of isolated OCT4 peptides, each said OCT4 peptide consisting of a peptide selected from the group consisting of SEQ ID NO: 53 and SEQ ID NO: 74, and further comprising an adjuvant, and one or more pharmaceutically acceptable excipients.

4. The composition of claim 3, wherein the plurality of OCT4 peptides comprises a peptide consisting of SEQ ID NO: 53 and a peptide consisting of SEQ ID NO:74.

* * * * *